US006723550B1

(12) United States Patent
Estell

(10) Patent No.: US 6,723,550 B1
(45) Date of Patent: Apr. 20, 2004

(54) PROTEASES FROM GRAM-POSITIVE ORGANISMS

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/462,845

(22) PCT Filed: Jul. 14, 1998

(86) PCT No.: PCT/US98/14647

§ 371 (c)(1),
(2), (4) Date: Jan. 13, 2000

(87) PCT Pub. No.: WO99/03984

PCT Pub. Date: Jan. 28, 1999

(30) Foreign Application Priority Data

Jul. 15, 1997 (EP) ............................................ 97305232

(51) Int. Cl.[7] ............................ C12N 9/48; C12N 1/20; C12N 15/00; C12P 21/04; C07H 21/04

(52) U.S. Cl. ................. 435/212; 435/252.3; 435/320.1; 435/252.31; 435/71.1; 435/440; 536/23.2

(58) Field of Search ............................. 435/212, 252.3, 435/320.1, 252.31, 71.1, 440, 219, 69.1; 536/23.2

(56) References Cited

U.S. PATENT DOCUMENTS

| | | | | |
|---|---|---|---|---|
| 3,817,837 A | 6/1974 | Rubenstein et al. | ..... | 195/103.5 |
| 3,850,752 A | 11/1974 | Schuurs et al. | .......... | 195/103.5 |
| 3,939,350 A | 2/1976 | Kronick et al. | ............. | 250/365 |
| 3,996,345 A | 12/1976 | Ullman et al. | ................ | 424/12 |
| 4,261,868 A | 4/1981 | Hora et al. | ................. | 252/529 |
| 4,275,149 A | 6/1981 | Litman et al. | ................. | 435/7 |
| 4,277,437 A | 7/1981 | Maggio | ....................... | 422/61 |
| 4,366,241 A | 12/1982 | Tom et al. | ..................... | 435/7 |
| 4,404,128 A | 9/1983 | Anderson | .................. | 252/546 |
| 4,533,359 A | 8/1985 | Kondo et al. | .................. | 8/128 |
| 4,816,567 A | 3/1989 | Cabilly et al. | .............. | 530/387 |
| 5,147,642 A | 9/1992 | Lotz et al. | ............... | 424/94.61 |
| 5,204,015 A | 4/1993 | Caldwell et al. | ....... | 252/174.12 |

(List continued on next page.)

FOREIGN PATENT DOCUMENTS

| | | |
|---|---|---|
| EP | 0 134 267 B1 | 8/1989 |
| EP | 0 344 250 B1 | 5/1993 |
| EP | 0 369 817 B1 | 4/1996 |
| WO | WO 88/06623 | 9/1988 |
| WO | WO 95/14099 | 5/1995 |

OTHER PUBLICATIONS

Sloma et al. Gene encoding a minor extracellular protease in *Bacillus subtilis*. Journal of Bacteriology, Dec. 1988, p. 5557–5563.*

Band et al. Construction and properties of an intracellular serine protease mutant of *Bacillus subtilis*. Journal of Bacteriology, Jan. 1987, p. 444–446.*

Kunst et al. SwissProt database—Accession P39839 (Feb. 1995).*

(List continued on next page.)

*Primary Examiner*—Ponnathapu Achutamurthy
*Assistant Examiner*—Yong D Pak
(74) *Attorney, Agent, or Firm*—Genencor International, Inc.

(57) ABSTRACT

The present invention relates to the identification of novel serine proteases in Gram-positive microorganisms. The present invention provides the nucleic acid and amino acid sequences for the *Bacillus subtilis* serine proteases SP1, SP2, SP3, SP4 and SP5. The present invention also provides host cells having a mutation or deletion of part or all of the gene encoding SP1, SP2, SP3, SP4 and SP5. The present invention also provides host cells further comprising nucleic acid encoding desired heterologous proteins such as enzymes. The present invention also provides a cleaning composition comprising a serine protease of the present invention.

12 Claims, 16 Drawing Sheets

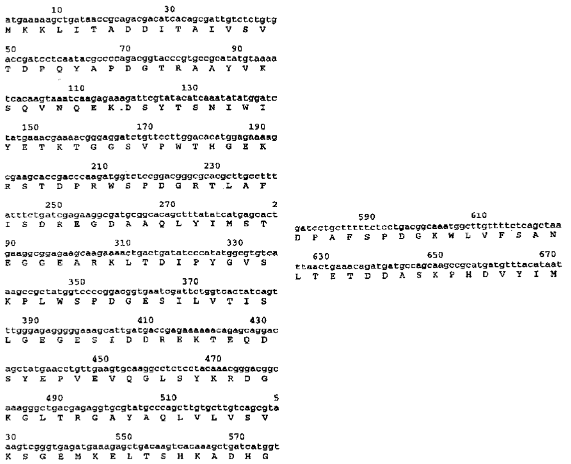

U.S. PATENT DOCUMENTS

| | | | | | |
|---|---|---|---|---|---|
| 5,264,366 | A | | 11/1993 | Ferrari et al. | 435/252.31 |
| 5,314,692 | A | | 5/1994 | Haarasilta et al. | 424/94.2 |
| 5,429,950 | A | * | 7/1995 | Power et al. | 435/252.31 |
| 5,585,253 | A | | 12/1996 | Doi et al. | 435/172.3 |
| 5,612,055 | A | | 3/1997 | Bedford et al. | 424/442 |
| 5,877,001 | A | * | 3/1999 | Murphy et al. | 435/227 |

OTHER PUBLICATIONS

Nakamura et al. Use of a triple protease–deficient mutant of *Bacillus subtilis* as a host for secretion of a *B. subtilis* cellulase and TEM B–lactamase.*

RD 21634, Apr. 1982.

Ausubel et al., ed. *Current Protocols in Molecular Biology*, John Wiley & Sons, Inc. Ch. 2 and 3, 1987.

Bakhiet et al., "Studies on Transfection and Transformation of Protoplasts if *Bacillus larvae, Bacillus subtilis*, and *Bacillus popilliae," Applied and Environmental Microbiology*, vol. 49, No. 3, pp. 577–581, Mar., 1985.

Benton et al., "Steering λgf Recombinant Clones by Hybridization to Single Plaques in situ," *Science*, vol. 196, No. 4286, pp. 180–182, Apr. 8, 1977.

Berger and Kimmel, "Guide to Molecular Cloning Techniques," *Methods in Enzymology*, Academic Press, San Diego, CA vol. 152, 1987.

Chang et al., "High Frequency Transformation of *Bacillus subtilis* Protoplasts by Plasmid DNA," *Molec. Gen. Genet.*, vol. 168, pp. 111–115, 1979.

Contente et al., "Marker Rescue Transformation by Linear Plasmid DNA in *Bacillus subitilis," Plasmid*, vol. 2, pp. 555–571, 1979.

Coombs, J., *Dictionary of Biotechnology*, Stockton Press, New York, N.Y., 1994.

Dieffenbach et al., *PCR Primer, a Laboratory Manual*, Cold Springs Harbor Press, Plainview, N.Y., 1995.

Fischer et al., "Introduction of plasmid pC 194 into *Bacillus thuringiensis* by Protoplast transformation and plasmid transfer," *Archives of Microbiology*, vol. 139, pp. 213–217, 1984.

Glover, D. M. ed., *DNA Cloning: A Practical Approach*, MRL Press, Ltd., Oxford, U.K., vol. I, II.

Grunstein et al., "Colony hybridization: A method for the isolation of cloned DNAs that contain a specific gene," *Proc. Natl. Acad. Sci. USA*, vol. 72, No. 10, pp. 3961–3965, Oct., 1975.

Haima, Peter et al., "Novel plasmid marker rescue transformation system for molecular cloning in *Bacillus subtilis* enabling direct selection of recombinants," *Mol. Gen. Genet.*, vol. 223, pp. 185–191, 1990.

Hampton, R. et al., *Serological Methods, a Laboratory Manual*, APS Press, St. Paul, MN 1990.

Harwood et al., *Molecular Biological Methods for Bacillus*, John Wiley & Sons, 1990.

Holubova et al., "Transfer of Liposome–Encapsulated Plasmid DNA to *Bacillus subtilis* Protoplasts and Calcium–Treated *Escherichia coli* Cells," *Folia Microbiol.*, vol. 30, pp. 97–100, 1985.

Kroli et al., "A Multifunctional Prokaryotic Protein Expression System: Overproduction, Affinity Purification, and Selective Detection," *DNA and Cell Biology*, vol. 12, No. 5, pp. 441–453, 1993.

Kunst, F. et al., "The complete genome sequences of the Gram–positive bacterium *Bacillus subtilis," Nature*, vol. 390, pp. 249–264, Nov. 20, 1997.

Levine, A. et al., "A 10–3 kbp segment from nprB to argJ at the 102° region of the *Bacillus subtilis* chormosome," *Microbiology*, vol. 143, pp. 175–177, 1997.

Maddox et al., "Elevated Serum Levels in Human Pregnancy of a Molecule Immunochemically Similar to Eosinophil Granule Major Basic Protein," *J. Exp. Med.*, vol. 158, pp. 1211–1226, Oct., 1983.

Mann et al., "Transformation of *Bacillus spp.*: an Examination of the Transformation of Bacillus Protoplasts by Plasmids pUB110 and pHV33," *Current Microbiology*, vol. 13, pp. 191–195, 1986.

Margot, Philippe et al., "The wprA gene of *Bacillus subtilis* 168, expressed during exponential growth, encodes a cell–wall–associated protease," Microbiology, vol. 142, pp. 3437–3444, 1996.

McDonald et al., "Plasmid Transformation of *Bacillus sphaericus* 1593," *Journal of General Microbiology*, vol. 130, pp. 203–208, 1984.

Murray et al., "Codon usage in plant genes," Nucleic Acids Research, vol. 17, No. 2, pp. 477–498, 1989.

Porath, Jerker "Immobilized Metal Ion Affinity Chromatography," *Protein Expression and Purification*, vol. 3, pp. 263–281, 1992.

Sambrook, J. et al., Molecular Cloning, A Laboratory Manual, $2^{nd}$ ed. Cold Spring Harbor Laboratory Press, Ch. 1–4, 1989.

Smith, Michael et al., "Protoplast Transformation in Coryneform Bacteria and Introduction of an α–Amylase Gene from *Bacillus amyloliquefaciens* into *Brevibacterium lactofermentum*," Applied and Environmental Microbiology, vol. 51, No. 3, pp. 634–639, Mar., 1986.

Vorobjeva, I.P. et al., "Transformation of *Bacillus megaterium* Protoplasts by Plasmid DNA," *FEMS Microbiology Letters* 7, pp. 261–263, 1980.

Ward, Michael et al., "Use of Aspergillus overproducing mutants, cured for integrated plasmid, to overproduce heterologous proteins," Appl. Microbiol. Biotechnol., vol. 39, pp. 738–743, 1993.

Weinrauch et al., "Plasmid Marker Rescue Transformation Proceeds by Breakage–Reunion in *Bacillus subtilis," Journal of Bacteriology*, vol. 169, No. 3, pp. 1205–1211, Mar., 1987.

Weinrauch et al., "Plasmid Marker Rescue Transformation in *Bacillus subtilis," Journal of Bacteriology*, vol. 154, No. 3, pp. 1077–1087, Jun., 1983.

EMBL/Genbank/DDBJ Databases Accession No. P70948, XP–0020808814, Feb. 1, 1997.

EMBL/Genbank/DDBJ Databases Accession No. 032120, Sequences reference 032120, XP–002080815, Jan. 1, 1998.

PCT International Search Report.

* cited by examiner

```
        10                            30
atgaaaaagctgataaccgcagacgacatcacagcgattgtctctgtg
M  K  K  L  I  T  A  D  D  I  T  A  I  V  S  V

50                         70                         90
accgatcctcaatacgccccagacggtacccgtgccgcatatgtaaaa
T  D  P  Q  Y  A  P  D  G  T  R  A  A  Y  V  K

             110                          130
tcacaagtaaatcaagagaaagattcgtatacatcaaatatatggatc
S  Q  V  N  Q  E  K  D  S  Y  T  S  N  I  W  I

    150                        170                        190
tatgaaacgaaaacgggaggatctgttccttggacacatggagaaaag
Y  E  T  K  T  G  G  S  V  P  W  T  H  G  E  K

                   210                        230
cgaagcaccgacccaagatggtctccggacgggcgcacgcttgccttt
R  S  T  D  P  R  W  S  P  D  G  R  T  L  A  F

         250                         270                 2
atttctgatcgagaaggcgatgcggcacagctttatatcatgagcact
I  S  D  R  E  G  D  A  A  Q  L  Y  I  M  S  T

90                        310                        330
gaaggcggagaagcaagaaaactgactgatatcccatatggcgtgtca
E  G  G  E  A  R  K  L  T  D  I  P  Y  G  V  S

             350                          370
aagccgctatggtccccggacggtgaatcgattctggtcactatcagt
K  P  L  W  S  P  D  G  E  S  I  L  V  T  I  S

    390                        410                        430
ttgggagagggggaaagcattgatgaccgagaaaaaacagagcaggac
L  G  E  G  E  S  I  D  D  R  E  K  T  E  Q  D

                   450                        470
agctatgaacctgttgaagtgcaaggcctctcctacaaacgggacggc
S  Y  E  P  V  E  V  Q  G  L  S  Y  K  R  D  G

         490                         510                 5
aaagggctgacgagaggtgcgtatgcccagcttgtgcttgtcagcgta
K  G  L  T  R  G  A  Y  A  Q  L  V  L  V  S  V

30                        550                        570
aagtcgggtgagatgaaagagctgacaagtcacaaagctgatcatggt
K  S  G  E  M  K  E  L  T  S  H  K  A  D  H  G
```

FIG._1A-1

590 610
gatcctgcttttctcctgacggcaaatggcttgttttctcagctaat
D P A F S P D G K W L V F S A N 630 650 670
ttaactgaaacagatgatgccagcaagccgcatgatgtttacataatg
L T E T D D A S K P H D V Y I M

FIG._1A-2

690 710
tcactggagtctggagatcttaagcaggttacacctcatcgcggctca
S L E S G D L K Q V T P H R G S 730 750 7
ttcggatcaagctcattttcaccagacggaaggtatcttgctttgctt
F G S S S F S P D G R Y L A L L 70 790 810
ggaaatgaaaaggaatataagaatgctacgctctcaaaggcgtggctc
G N E K E Y K N A T L S K A W L 830 850
tatgatatcgaacaaggccgcctcacatgtcttactgagatgctggac
Y D I E Q G R L T C L T E M L D 870 890 910
gttcatttagcggatgcgctgattggagattcattgatcggtggtgct
V H L A D A L I G D S L I G G A 930 950
gaacagcgcccgatttggacaaaggacagccaagggttttatgtcatc
E Q R P I W T K D S Q G F Y V I 970 990 10
ggcacagatcaaggcagtacgggcatctattatatttcgattgaaggc
G T D Q G S T G I Y Y I S I E G 10 1030 1050
cttgtgtatccgattcgtctggaaaaagagtacatcaatagcttttct
L V Y P I R L E K E Y I N S F S 1070 1090
ctttcacctgatgaacagcactttattgccagtgtgacaaagccggac
L S P D E Q H F I A S V T K P D

FIG._1B-1

```
 1110                            1130                            1150
agaccgagtgagctttacagtatcccgcttggacaggaagagaaacag
R   P   S   E   L   Y   S   I   P   L   G   Q   E   E   K   Q

                       1170                            1190
ctgactggcgcgaatgacaagtttgtcagggagcatacgatatcaata
L   T   G   A   N   D   K   F   V   R   E   H   T   I   S   I

          1210                            1230                           12
cctgaagagattcaatatgctacagaagacggcgtgatggtgaacggc
P   E   E   I   Q   Y   A   T   E   D   G   V   M   V   N   G

50                            1270                            1290
tggctgatgaggcctgcacaaatggaaggtgagacaacatatccactt
W   L   M   R   P   A   Q   M   E   G   E   T   T   Y   P   L

                1310                            1330
attcttaacatacacggcggtccgcatatgatgtacggacatacatat
I   L   N   I   H   G   G   P   H   M   M   Y   G   H   T   Y

 1350                            1370                            1390
tttcatgagtttcaggtgctggcggcgaaaggatacgcggtcgtttat
F   H   E   F   Q   V   L   A   A   K   G   Y   A   V   V   Y
```

FIG._1B-2

```
                       1410                            1430
atcaatccgagaggaagccacggctacgggcaggaatttgtgaatgcg
I   N   P   R   G   S   H   G   Y   G   Q   E   F   V   N   A

          1450                            1470                           14
gtcagaggagattatgggggaaaggattatgacgatgtgatgcaggct
V   R   G   D   Y   G   G   K   D   Y   D   D   V   M   Q   A

90                            1510                            1530
gtggatgaggctatcaaacgagatccgcatattgatcctaagcggctc
V   D   E   A   I   K   R   D   P   H   I   D   P   K   R   L

                1550                            1570
ggtgtcacgggcggaagctacggaggttttatgaccaactggatcgtc
G   V   T   G   G   S   Y   G   G   F   M   T   N   W   I   V

 1590                            1610                            1630
gggcagacgaaccgctttaaagctgccgttacccagcgctcgatatca
G   Q   T   N   R   F   K   A   A   V   T   Q   R   S   I   S
```

FIG._1C-1

```
              1650                            1670
aattggatcagctttcacggcgtcagtgatatcggctatttctttaca
N   W   I   S   F   H   G   V   S   D   I   G   Y   F   F   T

        1690                        1710                    17
gactggcagcttgagcatgacatgtttgaggacacagaaaagctctgg
D   W   Q   L   E   H   D   M   F   E   D   T   E   K   L   W

30                    1750                        1770
gaccggtctcctttaaaatacgcagcaaacgtggagacaccgctttg
D   R   S   P   L   K   Y   A   A   N   V   E   T   P   L   L

            1790                        1810
atactgcatggcgagcgggatgaccgatgcccgatcgagcaggcggag
I   L   H   G   E   R   D   D   R   C   P   I   E   Q   A   E

  1830                      1850                        1870
cagctgtttatcgctctgaaaaaaatgggcaaggaaaccaagcttgtc
Q   L   F   I   A   L   K   K   M   G   K   E   T   K   L   V

              1890                        1910
cgttttccgaatgcatcgcacaatttatcacgcaccggacacccaaga
R   F   P   N   A   S   H   N   L   S   R   T   G   H   P   R

        1930                        1950                    19
cagcggatcaagcgcctgaattatatcagctcatggtttgatcaacat
Q   R   I   K   R   L   N   Y   I   S   S   W   F   D   Q   H

70
ctc
L
```

FIG._1C-2

```
               170       180       190       200       210       220
dap2_yeast  WRHSTFGSYFVYDKSSSSFEEIGNEVALAIWSPNSNDIAYVQDN-NIYIYSAISKKTIRA
                                           ::|:::  |||:::'|   |  |:  |
YUXL                  MKKLITADDITAIVSVTDPQYAPDGTRAAYVKSQVNQEKDSYTSNIWIYE
                              10        20        30        40        50

               230       240       250       260       270       280
dap2_yeast  VTNDGSSFLFNGKPDWVYEEEVFEDDKAAWWSPTGDYLAFLKIDESEVGEFIIPYYVQDE
            : : ||      | |:: |:    | :    ||| |  |||::  |::::::   | :: |
YUXL        TKTGGSV------P-WTHGEKRSTDPR---WSPDGRTLAFISDREGDAAQL---YIMSTE
                          60        70                  80        90

               290       300       310       320       330
dap2_yeast  KDIYPEMRSIKYPKSG---TPNPHAELWVYSMKDGTSFHPRISGNKKDG--SLLITEVTW
                :: :| |  |     :|: :: | : |: :| |:  |    :::|:   : :  :::
YUXL        GGEARKLTDIPYGVSKPLWSPDGESILVTISLGEGESIDDR-EKTEQDSYEPVEVQGLSY
            100       110       120       130        140       150

            340       350       360       370            380       390
dap2_yeast  VGNGNVLVKTTDRSSDILTVFLIDTIAKTSNVVRNE----SSNGGWWEITHNTLFIPANE
              :|: |:: :  :  :::|    :      ||: : :      | :| |   :: |    :  ::
YUXL        KRDGKGLTRGAYAQLVLVSVKSGEMKELTSHKADHGDPAFSPDGKWLVFSAN---LTETD
              160       170       180       190       200        210

               400       410           420           430       440
dap2_yeast  TFDRPHNGYVDILPIGGYN----HLAYFENSNSS---HYKTLTEGKWEVVNGPLA----F
              ::||: |:  |  |  :      | : | :|: |    :|.:|  :: |  |: |:    :
YUXL        DASKPHDVYIMSLESGDLKQVTPHRGSFGSSSFSPDGRYLALLGNEKEYKNATLSKAWLY
                220       230       240       250       260        270

                450       460       470       480       490        499
dap2_yeast  DSMENRLYFISTRKSSTERHVYYID-LRSPNEIIEVTDTSEDGVYDVSFSSGRRFGL--L
            |  ::||  ::    :       :    | | :  |    :    : :| | :: ::|    |:  :
YUXL        DIEQGRLTCLTEMLDVHLADALIGDSLIGGAEQRPIWTKDSQGFYVIGTDQGST-GIYYI
                280       290       300       310       320        330
```

FIG._2A

```
             500       510       520       530       540       550
dap2_yeast   TYKGPKVPYQKIVDFHSRKAEKCDKGNVLGKSLYHLEKNEVLTKILEDYAVPR-KSFREL
             : :|   | :   :: :  : : |: : :::      : :|:      |::|  :  ::|
YUXL         SIEGLVYPIRLEKEYINSFSLSPDEQHFIASVTKPDRPSEL-------YSIPLGQEEKQL
                   340       350       360       370                380

             560                           570       580       590       600
dap2_yeast   NLGKDEFGKD----------------ILVNSYEILPNDFDETLSDHYPVFFFAYGGPNSQ
             : ::|:| ::                ::||:: : | :::   :  ||:::  :|||: :
YUXL         TGANDKFVREHTISIPEEIQYATEDGVMVNGWLMRPAQMEGETT--YPLILNIHGGPH-M
               390       400       410       420       430       440

                   610       620       630       640       650       660
dap2_yeast   QVVKTFSVGFNEVVASQLNAIVVVVDGRGTGFKGQDFRSLVRDRLGDYEARDQISAAS-L
             :  :|:    | :|:|::  | || :: ||:   ||:| : ||   |  :   | ::|::
YUXL         MYGHTYFHEF-QVLAAKGYA-VVYINPRGSHGYGQEFVNAVRGDYGGKDYDDVMQAVDEA
                   450       460       470       480       490       500
                               ↓Ser
                   670       680       690       700       710       720
dap2_yeast   YGSLTFVDPQKISLFGWSYGGYLTLKTLEKDGGRHFKYGMSVAPVTDWRFYDSVYTERYM
                 :||:::::  | ||||::|    :  :  :  :|| :::   :::|  :  :|    |:
YUXL         IKRDPHIDPKRLGVTGGSYGGFMTNWIVGQTN--RFKAAVTQRSISNWISFHGVSDIGYF
                   510       520       530       540       550
                                                   Asp
                   730       740           750     ↓760       770
dap2_yeast   HTP-QENFDGYVES-SVHNVTALAQANR----FLLMHGTGDDNVHFQNSLKFLDLLDLNG
              |  |  : |  :  :: :: :  : |  |      :|::||  ||  :::: :::  |   |
YUXL         FTDWQLEHDMFEDTEKLWDRSPLKYAANVETPLLILHGERDDRCPIEQAEQLFIALKKMG
             560       570  ↓His  580       590       600       610
                 780       790       800       810
dap2_yeast   VENYDVHVFPDSDHSIRYHNANVIVFDKLLDWAKRAFDGQFVK
              |:  |: ||:::|::
YUXL         KETKLVR-FPNASHNLSRTGHPRQRIKRLNYISSWFDQHL
             620       630       640       650
```

FIG._2B

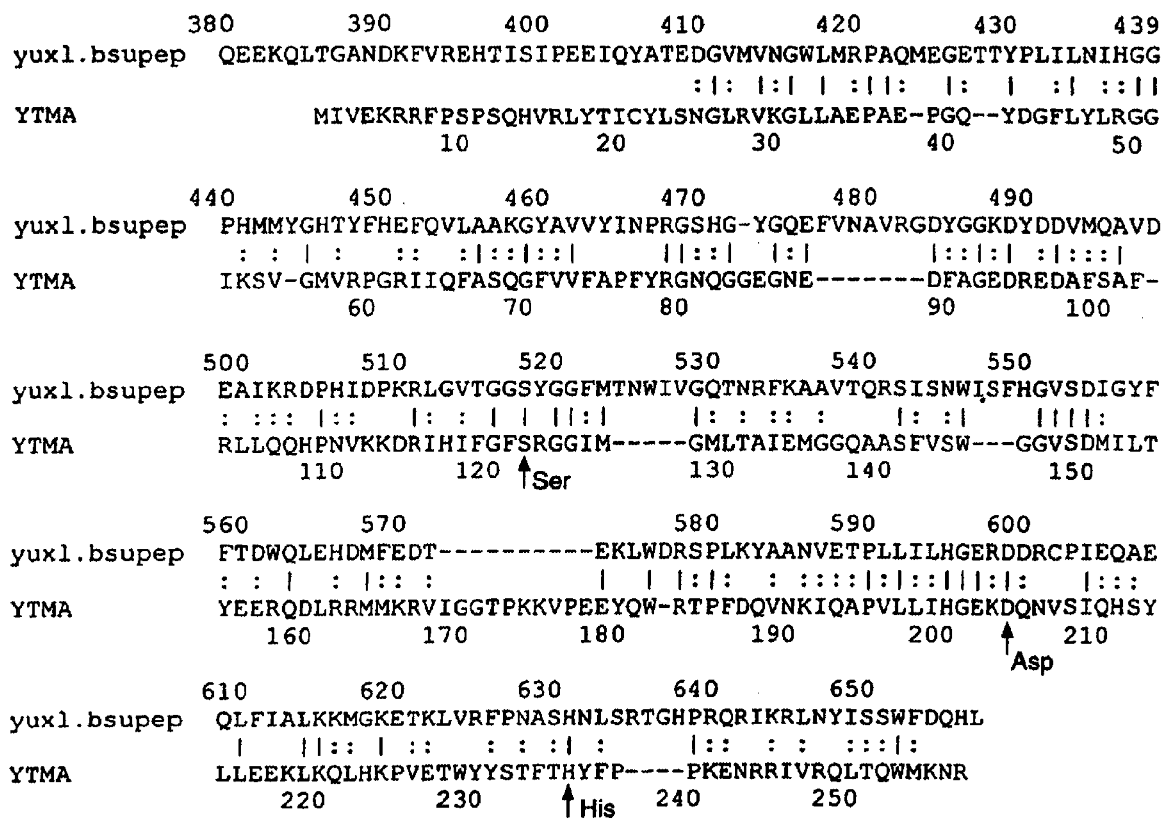

FIG._3

```
          380         390         400         410         420         430       439
yuxl.bsupep QEEKQLTGANDKFVREHTISIPEEIQYATEDGVMVNGWLMRPAQMEGETTYPLILNIHGG
            :|:  |:||   |  |::||:  |      |   |      ::|  ::|::||
YTMA                  MIVEKRRFPSPSQHVRLYTICYLSNGLRVKGLLAEPAE--PGQ---YDGFLYLRGG
                      1         10         20         30         40          50

          440         450         460         470         480         490
yuxl.bsupep PHMMYGHTYFHEFQVLAAKGYAVVYINPRGSHG--YGQEFVNAVRGDYGGKDYDDVMQAVD
            ::  ::    |:::::|  | |:::|| |:|   |::|  |     :|::| |:::::|
YTMA        IKSV-GMVRPGRIIQFASQGFVVFAPFYRGNQGGEGNE-----DFAGEDREDAFSAF-
            60         70         80         90                    100

          500         510         520         530         540         550
yuxl.bsupep EAIKRDPHIDPKRLGVTGGSYGGFMTNWIVGQTNRFKAAVTQRSISNWISFHGVSDIGYF
            : ::  ||  :|:|:| |::|  :|  |:   ::|      |||||:|||||||||
                                                        ↑Ser
YTMA        RLLQQHPNVKKDRIHIFGFSRGGIM-----GMLTAIEMGGQAASFVSW---GGVSDMLT
            110         120         130         140                150

          560         570         580         590         600
yuxl.bsupep FTDWQLEHDMFEDT----------EKLWDRSPLKYAANVETPLLILHGERDDRCPIEQAE
            |   ::     ::            :||::   |::   :|::|||||:|    |::|
                                                              ↑Asp
YTMA        YEERQDLRRMMKRVIGGTPKKVPEEYQW-RTPFDQVNKIQAPVLLIHGEKDQNVSIQHSY
            160         170         180         190         200         210

          610         620         630         640         650
yuxl.bsupep QLFIALKKMGKETKLVRFPNASHNLSRTGHPRQRIKRLNYISSWFDQHL
            |  ||:|:|   |::|  |:|   |:|    |::::|||:|
                                 ↑His
YTMA        LLEEKLKQLHKPVETWYYSTFTHYFP-----PKENRRIVRQLTQWMKNR
            220         230         240         250
```

FIG.\_3

```
                     410        420        430        440        450        460
yuxl.bsupep  PEEIQYATEDGVMVNGWLMRPAQMEGETTYPLILNIHGGPHMMYGHTYFHEFQVLAAKGY
                                             ||:: |||         |: :|   :|| ||:
YITV            MIQIENQTVSGIPFLHIVKEENRHRAVPLVIFIHGFTSAKE-HN-LHIAYLLAEKGF
                        10        20        30        40         50

                     470        480        490        500             510
yuxl.bsupep  AVVYINPRGSHGYGQEFVNAVRGDYGGKDYDDVMQAVDEA------IKRDPHIDPKRLGV
              :|   |:: | :|:: : :  : :|: :| |:: ::|       ::::  ||  |:|:
YITV         RAVL--PEALH-HGERGEEMAVEELAGHFWDIVLNEIEEIGVLKNHFEKEGLIDGGRIGL
                   60        70        80        90       100       110

                  520        530        540        550        560       570
yuxl.bsupep  TGGSYGGFMTNWIVGQTNRFKAAVTQRSISNWISFHGVSDIGYFFTDWQLEHDMFED-TE
             :| |:||: |    :   : :||:|:  :  |:: :   ::| :: : :| |: |: ::
YITV         AGTSMGGITTLGALTAYDWIKAGVSLMGSPNYVELFQ-QQIDHI-QSQGIEIDVPEEKVQ
               Ser↑ 120        130        140        150        160       170

                  580                 590        600        610        620
yuxl.bsupep  KLWDRSPLKYAANV-----ETPLLILHGERDDRCPIEQAEQLFIALKKMGKET----KLV
             :|  |  |:  :       : |||: || :|   |  ::::: ::|:  :|      :::
YITV         QLMKRLELRDLSLQPEKLQQRPLLFWHGAKDKVVPYAPTRKFYDTIKSHYSEQPERLQFI
                     180        190       200↑Asp  210        220       230

                630        640        650
yuxl.bsupep  RFPNASHNLSRTGHPRQRIKRLNYISSWFDQHL
               ||:|::      ||  :  |: |  ||: :|
YITV         GDENADHKV-----PRAAV--LKTIE-WFETYL
                  ↑His    240            250
```

FIG._4

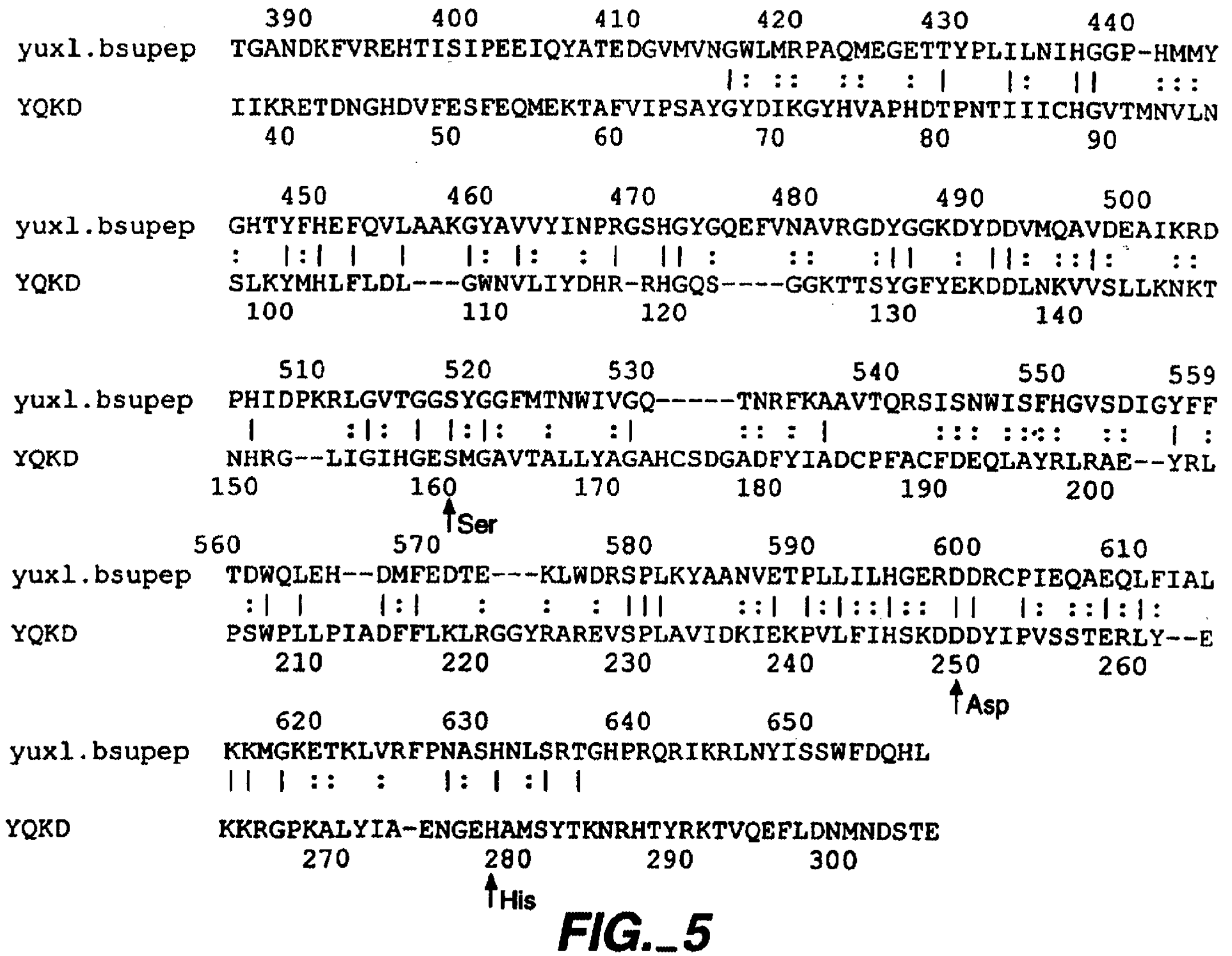

FIG._5

```
yux1.bsupep                       390         400        410          420           430         440
             TGANDKFVREHTISIPEEIQYATEDGVMVNGWLMRPAQMEGETTYPLILNIHGGP-HMMY
                   :|::  ::  ::   |  ::   :  :|   :|   :    |:   ::
YQKD         IIKRETDNGHDVFESFEQMEKTAFVIPSAYGYDIKGYHVAPHDTPNTIIICHGVTMNVLN
                  40          50         60          70         80          90

yux1.bsupep                450        460         470         480         490           500
             GHTYFHEFQVLAAKGYAVVYINPRGSHGYGQEFVNAVRGDYGGKDYDDVMQAVDEAIKRD
             :  |:: |:   |:: :   |    :|     |::   :: ||    ::   ::|:  ::
YQKD         SLKYMHLFLDL---GWNVLIYDHR-RHGQS------GGKTTSYGFYEKDDLNKVVSLLKNKT
                 100          110        120                130           140

yux1.bsupep           510        520         530         540         550       559
             PHIDPKRLGVTGGSYGGFMTNWIVGQ-----TNRFKAAVTQRSISNWISFHGVSDIGYFF
              |    ::|  | |:  :    ::     |   | :::  ::::  ::   :   |  :
YQKD         NHRG---LIGIHGESMGAVTALLYAGAHCSDGADFYIADCPFACFDEQLAYRLRAE--YRL
               150          160          170         180         190       200
                                           ↑Ser

yux1.bsupep           570        580         590         600         610
             TDWQLEH--DMFEDTE----KLWDRSPLKYAANVETPLLILHGERDDRCPIEQAEQLFIAL
             :  |  :::       ::     |::    ::  |  :|||::|:|:| |  :  ::|:|
YQKD         PSWPLLPIADFFLKLRGGYRAREVSPLAVIDKIEKPVLFIHSKDDDYIPVSSTERLY--E
               210         220         230         240         250         260
                                                                  ↑Asp

yux1.bsupep           620        630         640         650
             KKMGKETKLVRFPNASHNLSRTGHPRQRIKRLNYISSWEDQHL
             ||  :   :|:  |       :   :  :|   :|  ||
YQKD         KKRGPKALYIA-ENGEHAMSYTKNRHTYRKTVQEFLDNMNDSTE
               270         280          290         300
                                ↑His

                            FIG._5
```

```
                         330       340       350       360       370      379
yux1.bsupep   GTDQGSTGIYYISIEGLVYPIRLEKEYINSFSLSPDE-QHFIASVTKPDRPSELYSIPLG
                                                |:|  |: | :    | |   ||:::: |
CAH                                             MQLFDLPLDQLQTYKPEKTAPKDFSEFWKLSLE
                                                          10        20        30

              380       390       400       410       420       430
yux1.bsupep   QEEKQLTGANDKFVREHTISIP-EEIQYATEDGVMVNGWLMRPAQMEGETTYPLILNIHG
              :  |  :  : : |   : ::   :: | :  :: ::||   | : ||   :| |:: ||
CAH           ELAKVQAEPDLQPVDYPADGVKVYRLTYKSFGNARITGWYAVPDK-EGP--HPAIVKYHG
                   40        50        60        70        80        90

               440       450       460                 470       480
yux1.bsupep   GPHMMYGHTYFHEFQVLAAKGYAV-------------VYINPRGSHGYGQEFVNAVRGD-
                  : |:  :||:   | :|||:              : |:|:| |: |     : :  |
CAH           YNASYDGE--IHEMVNWALHGYATFGMLVRGQQSSEDTSISPHG-HALGWMTKGILDKDT
                        100       110       120       130       '140

                    490       500       510       520       530       540
yux1.bsupep   --YGGKDYDDVMQAVDEAIKRDPHIDPKRLGVTGGSYGGFMTNWIVGQTNRFKAAVTQRS
                | |  | |:::|: |:|:   ::|  |:||||| || :|   :: ::  ||||::
CAH           YYYRGV-YLDAVRAL-EVISSFDEVDETRIGVTGGSQGGGLTIAAAALSDIPKAAVADYP
              150       160       170       180↑Ser   190       200

                     550                 560       570       580       590
yux1.bsupep   -ISNWISFHGVS------DIGYFFTDWQLEHDMFEDTEKLWDRSPLKYAANVETPLLILH
                :||:      |:       :|: ||        :   :  : |   : :: |  |::|:|:
CAH           YLSNFERAIDVALEQPYLEINSFFRRNGSPETEVQAMKTLSYFDIMNLADRVKVPVLMSI
                  210       220       230       240       250       260

                  600       610       620       630       640       650
yux1.bsupep   GERDDRCPIEQAEQLFIALKKM--GKETKLVRFPNASHNLSRTGHPRQRIKRLNYISSWF
              |  |   |        :| | :::    || |: |:
CAH           GLIDKVTP---PSTVFAAYNHLETKKELKVYRYFGHEYIPAFQTEKLAFFKQHLKG
                  270       280       290       300       310
                  ↑Asp                          ↑His
```

FIG._6

```
        10                  30
ttgattgtagagaaaagaagatttccgtcgccaagccagcatgtgcgt
L  I  V  E  K  R  R  F  P  S  P  S  Q  H  V  R

50                  70                  90
ttgtatacgatctgctatctgtcaaatggattacgggttaaggggctt
L  Y  T  I  C  Y  L  S  N  G  L  R  V  K  G  L

           110                 130
ctggctgagccggcggaaccgggacaatatgacggatttttatatttg
L  A  E  P  A  E  P  G  Q  Y  D  G  F  L  Y  L

   150                 170                 190
cgcggcgggattaaaagcgtgggcatggttcggccgggccggattatc
R  G  G  I  K  S  V  G  M  V  R  P  G  R  I  I

               210                 230
cagtttgcatcccaagggtttgtggtgtttgctcctttttacagaggc
Q  F  A  S  Q  G  F  V  V  F  A  P  F  Y  R  G

       250                 270                 2
aatcaaggaggagaaggcaatgaggatttgccggagaagacagggag
N  Q  G  G  E  G  N  E  D  F  A  G  E  D  R  E

90                  310                 330
gatgcattttctgcttttcgcctgcttcagcagcacccaaatgtcaag
D  A  F  S  A  F  R  L  L  Q  Q  H  P  N  V  K

           350                 370
aaggatagaatccatatcttcggtttttcccgcggcggaattatggga
K  D  R  I  H  I  F  G  F  S  R  G  G  I  M  G

   390                 410                 430
atgctcactgcgatcgaaatgggcgggcaggcagcttcatttgtttcc
M  L  T  A  I  E  M  G  G  Q  A  A  S  F  V  S

               450                 470
tggggaggcgtcagtgatatgattcttacatacgaggagcggcaggat
W  G  G  V  S  D  M  I  L  T  Y  E  E  R  Q  D

       490                 510                 5
ttgcggcgaatgatgaaaagagtcatcggcggaacaccgaaaaaggtg
L  R  R  M  M  K  R  V  I  G  G  T  P  K  K  V

30                  550                 570
cctgaggaatatcaatggaggacaccgtttgaccaagtaaacaaaatt
P  E  E  Y  Q  W  R  T  P  F  D  Q  V  N  K  I
```

FIG._7A

```
           590                         610
caggctcccgtgctgttaatccatggagaaaaagaccaaaatgtttcg
 Q   A   P   V   L   L   I   H   G   E   K   D   Q   N   V   S

      630                    650                       670
attcagcattcctatttattagaagagaagctaaaacaactgcataag
 I   Q   H   S   Y   L   L   E   E   K   L   K   Q   L   H   K

            690        ·           710
ccggtggaaacatggtactacagtacattcacacattatttcccgcca
 P   V   E   T   W   Y   Y   S   T   F   T   H   Y   F   P   P

        730                  750                          7
aaagaaaaccggcgtatcgtgcggcagctcacacaatggatgaaaaac
 K   E   N   R   R   I   V   R   Q   L   T   Q   W   M   K   N

70
cgc
 R
```

FIG._7B

```
        10                    30
gtgatacaaattgagaatcaaaccgtttccggtattccgtttttacat
V  I  Q  I  E  N  Q  T  V  S  G  I  P  F  L  H

50                     70                    90
attgtaaaggaagagaacaggcaccgcgctgttcctctcgtgatcttt
I  V  K  E  E  N  R  H  R  A  V  P  L  V  I  F

           110                   130
atacatggttttacaagcgcgaaggaacacaaccttcatattgcttat
I  H  G  F  T  S  A  K  E  H  N  L  H  I  A  Y

   150                    170                   190
ctgcttgcggagaagggttttagagccgttctgccggaggctttgcac
L  L  A  E  K  G  F  R  A  V  L  P  E  A  L  H

                 210                   230
catggggaacggggagaagaaatggctgttgaagagctggcggggcat
H  G  E  R  G  E  E  M  A  V  E  E  L  A  G  H

       250                   270                   2
ttttgggatatcgtcctcaacgagattgaagagatcggcgtacttaaa
F  W  D  I  V  L  N  E  I  E  E  I  G  V  L  K

90                     310                   330
aaccatttttgaaaaagagggcctgatagacggcggccgcatcggtctc
N  H  F  E  K  E  G  L  I  D  G  G  R  I  G  L

           350                   370
gcaggcacgtcaatgggcggcatcacaacgcttggcgctttgactgca
A  G  T  S  M  G  G  I  T  T  L  G  A  L  T  A

   390                    410                   430
tatgattggataaaagccggcgtcagcctgatgggaagcccgaattac
Y  D  W  I  K  A  G  V  S  L  M  G  S  P  N  Y

                 450                   470
gtggagctgtttcagcagcagattgaccatattcaatctcagggcatt
V  E  L  F  Q  Q  Q  I  D  H  I  Q  S  Q  G  I

       490                   510                   5
gaaatcgatgtgccggaagagaaggtacagcagctgatgaaacgtctc
E  I  D  V  P  E  E  K  V  Q  Q  L  M  K  R  L

30                     550                   570
gagttgcgggatctcagccttcagccggagaaactgcaacagcgcccg
E  L  R  D  L  S  L  Q  P  E  K  L  Q  Q  R  P
```

FIG._8A

```
             590                                 610
cttttattttggcacggcgcaaaagataaagttgtgccttacgcgccg
L  L  F  W  H  G  A  K  D  K  V  V  P  Y  A  P

   630                    650                      670
acccggaaattttatgacacgattaaatcccattacagcgagcagccg
T  R  K  F  Y  D  T  I  K  S  H  Y  S  E  Q  P

                      690                     710
gaacgcctgcaatttatcggagatgaaaacgctgaccataaagtcccg
E  R  L  Q  F  I  G  D  E  N  A  D  H  K  V  P

          730                     750
cgggcagctgtgttaaaaacgattgaatggtttgaaacgtactta
R  A  A  V  L  K  T  I  E  W  F  E  T  Y  L
```

FIG._8B

```
              10                        30
ttgaagaaaatccttttggccattggcgcgctcgtaacagctgtcatc
 L  K  K  I  L  L  A  I  G  A  L  V  T  A  V  I

         50              70               90
gcaatcggaattgttttttcacatatgattctattcatcaagaaaaaa
 A  I  G  I  V  F  S  H  M  I  L  F  I  K  K  K

              110                       130
acggatgaagacattatcaaaagagagacagacaacggacatgatgtg
 T  D  E  D  I  I  K  R  E  T  D  N  G  H  D  V

         150                   170               190
tttgaatcatttgaacaaatggagaaaaccgcttttgtgataccctcc
 F  E  S  F  E  Q  M  E  K  T  A  F  V  I  P  S

                   210                       230
gcttacgggtacgacataaaaggataccatgtcgcaccgcatgacaca
 A  Y  G  Y  D  I  K  G  Y  H  V  A  P  H  D  T

              250                       270              2
ccaaataccatcatcatctgccacggggtgacgatgaatgtactgaat
 P  N  T  I  I  I  C  H  G  V  T  M  N  V  L  N

90                  310                       330
tctcttaagtatatgcatttatttctagatctcggctggaatgtgctc
 S  L  K  Y  M  H  L  F  L  D  L  G  W  N  V  L

              350                       370
atttatgaccatcgccggcatggccaaagcggcggaaagacgaccagc
 I  Y  D  H  R  R  H  G  Q  S  G  G  K  T  T  S

         390                   410                  430
tacgggttttacgaaaaggatgatctcaataaggttgtcagcttgctc
 Y  G  F  Y  E  K  D  D  L  N  K  V  V  S  L  L

                   450                       470
aaaaacaaaacaaatcatcgcggattgatcggaattcatggtgagtcg
 K  N  K  T  N  H  R  G  L  I  G  I  H  G  E  S

              490                       510              5
atgggggccgtgaccgccctgctttatgctggtgcacactgcagcgat
 M  G  A  V  T  A  L  L  Y  A  G  A  H  C  S  D

30                  550                       570
ggcgctgatttttatattgccgattgtccgttcgcatgttttgatgaa
 G  A  D  F  Y  I  A  D  C  P  F  A  C  F  D  E
```

FIG._9A

```
             590                                   610
cagcttgcctatcggctgagagcggaatacaggctcccgtcttggccc
Q  L  A  Y  R  L  R  A  E  Y  R  L  P  S  W  P

    630                         650                         670
ctgcttcctatcgccgacttctttttgaagctgaggggaggctatcgc
L  L  P  I  A  D  F  F  L  K  L  R  G  G  Y  R

                        690                         710
gcacgtgaagtatctccgcttgctgtcattgataaaattgaaaagccg
A  R  E  V  S  P  L  A  V  I  D  K  I  E  K  P

          730                         750                         7
gtcctctttattcacagtaaggatgatgactacattcctgtttcttca
V  L  F  I  H  S  K  D  D  D  Y  I  P  V  S  S

70                          790                         810
accgagcggctttatgaaaagaaacgcggtccgaaagcgctgtacatt
T  E  R  L  Y  E  K  K  R  G  P  K  A  L  Y  I

             830                         850
gccgagaacggtgaacacgccatgtcatataccaaaaatcggcatacg
A  E  N  G  E  H  A  M  S  Y  T  K  N  R  H  T

    870                         890                         910
taccgaaaaacagtgcaggagtttttagacaacatgaatgattcaaca
Y  R  K  T  V  Q  E  F  L  D  N  M  N  D  S  T
```

*FIG._9B*

PROTEASES FROM GRAM-POSITIVE ORGANISMS

This application is a national application under 35 U.S.C. section 371 of International Application No. PCT/US98/14647, having an international filing date of Jul. 14, 1998.

FIELD OF THE INVENTION

The present invention relates to serine proteases derived from gram-positive microorganisms. The present invention provides nucleic acid and amino acid sequences of serine protease 1, 2, 3, 4 and 5 identified in Bacillus. The present invention also provides methods for the production of serine protease 1, 2, 3, 4 and 5 in host cells as well as the production of heterologous proteins in a host cell having a mutation or deletion of part or all of at least one of the serine proteases of the present invention.

BACKGROUND OF THE INVENTION

Gram-positive microorganisms, such as members of the group Bacillus, have been used for large-scale industrial fermentation due, in part, to their ability to secrete their fermentation products into the culture media. In gram-positive bacteria, secreted proteins are exported across a cell membrane and a cell wall, and then are subsequently released into the external media usually maintaining their native conformation.

Various gram-positive microorganisms are known to secrete extracellular and/or intracellular protease at some stage in their life cycles. Many proteases are produced in large quantities for industrial purposes. A negative aspect of the presence of proteases in gram-positive organisms is their contribution to the overall degradation of secreted heterologous or foreign proteins.

The classification of proteases found in microorganisms is based on their catalytic mechanism which results in four groups: the serine proteases; metalloproteases; cysteine proteases; and aspartic proteases. These categories can be distinguished by their sensitivity to various inhibitors. For example, the serine proteases are inhibited by phenylmethylsulfonylfluoride (PMSF) and diisopropylfluorophosphate (DIFP); the metalloproteases by chelating agents; the cysteine enzymes by iodoacetamide and heavy metals and the aspartic proteases by pepstatin. The serine proteases have alkaline pH optima, the metalloproteases are optimally active around neutrality, and the cysteine and aspartic enzymes have acidic pH optima (*Biotechnology Handbooks, Bacillus*. vol. 2, edited by Harwood, 1989 Plenum Press, New York).

Proteolytic enzymes that are dependent upon a serine residue for catalytic activity are called serine proteases. As described in Methods in Enzymology, vol. 244, Academic Press, Inc. 1994, page 21, serine proteases of the family S9 have the catalytic residue triad "Ser-Asp-His with conservation of amino acids around them.

SUMMARY OF THE INVENTION

The present invention relates to the unexpected discovery of five heretofore unknown or unrecognized S9 type serine proteases found in uncharacterized translated genomic nucleic acid sequences of *Bacillus subtilis*, designated herein as SP1, SP2, SP3, SP4 and SP5 having the nucleic acid and amino acid as shown in the Figures. The present invention is based, in part, upon the presence the amino acid triad S-D-H in the five serine proteases, as well as amino acid conservation around the triad. The present invention is also based in part upon the heretofore uncharacterized or unrecognized overall amino acid relatedness that SP1, SP2, SP3, SP4 and SP5 have with the serine protease dipeptidylamino peptidase B from yeast (DAP) and with each other.

The present invention provides isolated polynucleotide and amino acid sequences for SP1, SP2, SP3, SP4 and SP5. Due to the degeneracy of the genetic code, the present invention encompasses any nucleic acid sequence that encodes the SP1, SP2, SP3, SP4 and SP5 deduced amino acid sequences shown in FIGS. 2A–2B–FIG. 6, respectively.

The present invention encompasses amino acid variations of *B. subtilis* SP1, SP2, SP3, SP4 and SP5 disclosed herein that have proteolytic activity. *B. subtilis* SP1, SP2. SP3, SP4 and SP5, as well as proteolytically active amino acid variations thereof, have application in cleaning compositions. In one aspect of the present invention, SP1, SP2, SP3, SP4 and SP5 obtainable from a gram-positive microorganism are produced on an industrial fermentation scale in a microbial host expression system. In another aspect, isolated and purified SP1, SP2, SP3, SP4 or SP5 obtainable from a gram-positive microorganism is used in compositions of matter intended for cleaning purposes, such as detergents. Accordingly, the present invention provides a cleaning composition comprising at least one of SP1, SP2, SP3, SP4 and SP5 obtainable from a gram-positive microorganism. The serine protease may be used alone in the cleaning composition or in combination with other enzymes and/or mediators or enhancers.

The production of desired heterologous proteins or polypeptides in gram-positive microorganisms may be hindered by the presence of one or more proteases which degrade the produced heterologous protein or polypeptide. Therefore, the present invention also encompasses gram-positive microorganism having a mutation or deletion of part or all of the gene encoding SP1, SP2, SP3, SP4 and/or SP5, which results in the inactivation of their proteolytic activity, either alone or in combination with deletions or mutations of other proteases, such as apr, npr, epr, mpr for example, or other proteases known to those of skill in the art. In one embodiment of the present invention, the gram-positive organism is a member of the genus Bacillus. In another embodiment, the Bacillus is *Bacillus subtilis.*

In another aspect, the gram-positive microorganism host having one or more deletions or mutations in a serine protease of the present invention is further genetically engineered to produce a desired protein. In one embodiment of the present invention, the desired protein is heterologous to the gram-positive host cell. In another embodiment, the desired protein is homologous to the host cell. The present invention encompasses a gram-positive host cell having a deletion or interruption of the naturally occurring nucleic acid encoding the homologous protein, such as a protease, and having nucleic acid encoding the homologous protein or a variant thereof re-introduced in a recombinant form. In another embodiment, the host cell produces the homologous protein. Accordingly, the present invention also provides methods and expression systems for reducing degradation of heterologous or homologous proteins produced in gram-positive microorganisms comprising the steps of obtaining a Bacillus host cell comprising nucleic acid encoding said heterologous protein wherein said host cell contains a mutation or deletion in at least one of the genes encoding SP1, SP2, SP3, SP4 and SP5; and growing said Bacillus host cell under conditions suitable for the expression of said heterologous protein. The gram-positive microorganism may be normally sporulating or non-sporulating.

The present invention provides methods for detecting gram positive microorganism homologs of *B. subtilis* SP1, SP2, SP3, SP4 and SP5 that comprises hybridizing part or all of the nucleic acid encoding *B. subtilis* SP1, SP2, SP3, SP4 and SP5 with nucleic acid derived from gram-positive organisms, either of genomic or cDNA origin.

BRIEF DESCRIPTION OF THE DRAWINGS

FIGS. 1A–1C shows the DNA (SEQ ID NO:1) and deduced amino acid sequence (SEQ ID NO:2) for SP1 (YUXL).

FIGS. 2A–2B show an amino acid alignment between DAP (dap2_yeast) (SEQ ID NO:3) and SP1 (YUXL). For FIGS. 2A–2B, 3 and 4, the amino acid triad S-D-H is indicated.

FIG. 3 shows an amino acid alignment between SP1 (YUXL) (SEQ ID NO:2) and SP2 (YTMA) (SEO ID NO:5).

FIG. 4 shows and amino add alignment between SP1 (YUXL) (SEQ ID NO:2) and SP3 (YITV) (SEQ ID NO:7).

FIG. 5 shows and amino acid alignment between SP1 (YUXL) (SEQ ID NO:2) and SP4 (YQKD) (SEQ ID NO:9).

FIG. 6 shows and amino add alignment between SP1 (YUXL) (SEQ ID NO:2) and SP5 (CAH) (SEQ ID NO:10).

FIGS. 7A–7B shows the DNA (SEQ ID NO:4) and deduced amino acid sequence for SP2 (YTMA) (SEQ ID NO:5).

FIGS. 8A–8B shows the DNA (SEQ ID NO:6) and deduced amino acid sequence for SP3 (YITV) (SEQ ID NO:7).

FIGS. 9A–9B shows the DNA (SEQ ID NO:8) and deduced amino acid sequence for SP4 (YQKD) (SEQ ID NO:9).

DETAILED DESCRIPTION OF THE PREFERRED EMBODIMENTS

Definitions

As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus* and *B. thuringiensis.*

The present invention encompasses novel SP1, SP2, SP3, SP4 and SP5 from gram positive organisms. In a preferred embodiment, the gram-positive organisms is a Bacillus. In another preferred embodiment, the gram-positive organism is *Bacillus subtilis*. As used herein, "*B.subtilis* SP1 (YuxL) refers to the DNA and deduced amino acid sequence shown in FIGS. 1A–1C and FIGS. 2A–2B; SP2 (YtmA) refers to the DNA and deduced amino acid sequence shown in FIGS. 7A–7B and FIG. 3; SP3 (YitV) refers to the DNA and deduced amino acid sequence shown in FIGS. 8A–8B and FIG. 4; SP4 (YqkD) refers to the DNA and deduced amino acid sequence shown in FIGS. 9A–9B and FIG. 5; and SP5 (CAH) refers to the deduced amino acid sequence shown in FIG. 6. The present invention encompasses amino acid variations of the *B.subtilis* amino acid sequences of SP1, SP2, SP3, SP4 and SP5 that have proteolytic activity. Such proteolytic amino acid variants can be used in cleaning compositions.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homolog" as used herein refers to a novel gram-positive microorganism polynucleotide that has at least 80%, at least 90% and at least 95% identity to *B.subtilis* SP1, SP2, SP3, SP4 or SP5, or which is capable of hybridizing to *B.subtilis* SP1, SP2, SP3, SP4 or SP5 under conditions of high stringency and which encodes an amino acid sequence having serine protease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases, cellulases, amylases, carbohydrases, and lipases; isomerases such as racemases, epimerases, tautomerases, or mutases; transferases, kineses and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein, or a variant thereof re-introduced in a recombinant form. In another embodiment, the host cell produces the homologous protein.

As used herein, the term "overexpressing" when referring to the production of a protein in a host cell means that the protein is produced in greater amounts than its production in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

Detailed Description of the Preferred Embodiments

The unexpected discovery of the serine proteases SP1, SP2, SP3, SP4 and SP5 in *B.subtilis* provides a basis for producing host cells, expression methods and systems which can be used to prevent the degradation of recombinantly produced heterologous proteins. In a preferred embodiment, the host cell is a gram-positive host cell that has a deletion or mutation in the naturally occurring serine protease said mutation resulting in the complete deletion or inactivation of the production by the host cell of the proteolytic serine protease gene product. In another embodiment of the present invention, the host cell is additionally genetically engineered to produced a desired protein or polypeptide.

It may also be desired to genetically engineer host cells of any type to produce a gram-positive serine protease SP1, SP2, SP3, SP4 or SP5. Such host cells are used in large scale fermentation to produce large quantities of the serine protease which may be isolated or purified and used in cleaning products, such as detergents.

I. Serine Protease Nucleic Acid and Amino Acid Sequences

The SP1, SP2, SP3 and SP4 polynucleotides having the sequences as shown in the Figures encode the *Bacillus*

*subtilis* serine SP1, SP2, SP3, and SP4. As will be understood by the skilled artisan, due to the degeneracy of the genetic code, a variety of polynucleotides can encode the Bacillus SP1, SP2, SP3, SP4 and SP5. The present invention encompasses all such polynucleotides.

The present invention encompasses novel SP1, SP2, SP3, SP4 and SP5 polynucleotide homologs encoding gram-positive microorganism serine proteases SP1, SP2, SP3, SP4 and SP5, respectively, which have at least 80%, or at least 90% or at least 95% identity to *B.subtilis* as long as the homolog encodes a protein that has proteolytic activity.

Gram-positive polynucleotide homologs of *B.subtilis* SP1, SP2, SP3, SP4 or SP5 may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA. Nucleic acid sequences derived from genomic DNA may contain regulatory regions in addition to coding regions. Whatever the source, the isolated serine protease gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the SP1, SP2, SP3, SP4 or SP5 may be accomplished in a number of ways. For example, a *B.subtilis* SP1, SP2, SP3, SP4 or SP5 gene of the present invention or its specific RNA, or a fragment thereof, such as a probe or primer, may be isolated and labeled and then used in hybridization assays to detect a gram-positive SP1, SP2, SP3, SP4 or SP5 gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram-positive SP1, SP2, SP3, SP4 or SP5 polynucleotide homologs which comprises hybridizing part or all of a nucleic acid sequence of *B. subtilis* SP1, SP2, SP3, SP4 or SP5 with gram-positive microorganism nucleic acid of either genomic or cDNA origin.

Also included within the scope of the present invention are gram-positive microorganism polynucleotide sequences that are capable of hybridizing to the nucleotide sequence of *B.subtilis* SP1, SP2, SP3, SP4 or SP5 under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) *Dictionary of Biotechnology*, Stockton Press, New York, N.Y.).

The process of amplification as carried out in polymerase chain reaction (PCR) technologies is described in Dieffenbach C W and G S Dveksler (1995, *PCR Primer, a Laboratory Manual*, Cold Spring Harbor Press, Plainview, N.Y.). A nucleic acid sequence of at least about 10 nucleotides and as many as about 60 nucleotides from *B. subtilis* SP1, SP2, SP3, SP4 or SP5 preferably about 12 to 30 nucleotides, and more preferably about 20–25 nucleotides can be used as a probe or PCR primer.

The *B.subtilis* amino acid sequences SP1, SP2, SP3, SP4 and SP5 (shown in FIGS. 2A–2B through FIG. 6) were identified via a FASTA search of *Bacillus subtilis* genomic nucleic acid sequences. *B. subtilis* SP1 (YuxL) was identified by its structural homology to the serine protease DAP classified as an S9 type serine protease, designated in FIGS. 2A–2B as "dap2_yeast". As shown in FIGS. 2A–2B, SP1 has the amino acid dyad "S-D-H" indicated. Conservation of amino acids around each residue is noted in FIGS. 2A–2B through FIG. 6. SP2 (YtmA); SP3 (YitV) SP4 (YqkD) and SP5 (CAH) were identified upon by their structural and overall amino acid homology to SP1 (YuxL). SP1 and SP4 were described in Parsot and Kebayashi, respectively, but were not characterized as serine proteases or serine proteases of the S9 family.

II. Expression Systems

The present invention provides host cells, expression methods and systems for the enhanced production and secretion of desired heterologous or homologous proteins in gram-positive microorganisms. In one embodiment, a host cell is genetically engineered to have a deletion or mutation in the gene encoding a gram-positive SP1, SP2, SP3, SP4 or SP5 such that the respective activity is deleted. In an alternative embodiment of the present invention, a gram-positive microorganism is genetically engineered to produce a serine protease of the present invention.

Inactivation of a Gram-positive Serine Protease in a Host Cell

Producing an expression host cell incapable of producing the naturally occurring serine protease necessitates the replacement and/or inactivation of the naturally occurring gene from the genome of the host cell. In a preferred embodiment, the mutation is a non-reverting mutation.

One method for mutating nucleic acid encoding a gram-positive serine protease is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring, nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the serine protease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded serine protease gene. In another preferred embodiment, nucleic acid encoding the catalytic amino acid residues are deleted.

Deletion of the naturally occurring gram-positive microorganism serine protease can be carried out as follows. A serine protease gene including its 5' and 3' regions is isolated and inserted into a cloning vector. The coding region of the serine protease gene is deleted form the vector in vitro, leaving behind a sufficient amount of the 5' and 3' flanking sequences to provide for homologous recombination with the naturally occurring gene in the parent host cell. The vector is then transformed into the gram-positive host cell. The vector integrates into the chromosome via homologous recombination in the flanking regions. This method leads to a gram-positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the serine protease locus. Since illegitimate recombination will give different results it will be necessary to determine whether the complete gene has been deleted, such as through nucleic acid sequencing or restriction maps.

Another method of inactivating the naturally occurring serine protease gene is to mutagenize the chromosomal gene copy by transforming a gram-positive microorganism with oligonucleotides which are mutagenic. Alternatively, the chromosomal serine protease gene can be replaced with a mutant gene by homologous recombination.

The present invention encompasses host cells having additional protease deletions or mutations, such as deletions or mutations in apr, npr, epr, mpr and others known to those of skill in the art. U.S. Pat. No. 5,264,366 discloses Bacillius host cells having a deletion of apr and npr; U.S. Pat. No. 5,585,253 discloses Bacillus host cells having a deletion of epr; Margot et al., 1996, Microbiology 142: 3437–3444 disclose host cells having a deletion in wpr and EP patent 0369817 discloses Bacillus host cells having a deletion of mpr.

III. Production of Serine Protease

For production of serine protease in a host cell, an expression vector comprising at least one copy of nucleic acid encoding a gram-positive microorganism SP1, SP2, SP3, SP4 or SP5, and preferably comprising multiple copies, is transformed into the host cell under conditions suitable for expression of the serine protease. In accordance with the present invention, polynucleotides which encode a gram-positive microorganism SP1, SP2, SP3, SP4 or SP5, or fragments thereof, or fusion proteins or polynucleotide homolog sequences that encode amino acid variants of B. SP1, SP2, SP3, SP4 or SP5, may be used to generate recombinant DNA molecules that direct their expression in host cells. In a preferred embodiment, the gram-positive host cell belongs to the genus Bacillus. In another preferred embodiment, the gram positive host cell is *B. subtilis.*

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered SP1, SP2, SP3, SP4 or SP5 polynucleotide sequences which may be used in accordance with the invention include deletions, insertions or substitutions of different nucleotide residues resulting in a polynucleotide that encodes the same or a functionally equivalent SP1, SP2, SP3, SP4 or SP5 homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring SP1, SP2, SP3, SP4 or SP5.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally SP1, SP2, SP3, SP4 or SP5 variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine, serine, threonine, phenylalanine, and tyrosine.

The SP1, SP2, SP3, SP4 or SP5 polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a gram-positive microorganism SP1, SP2, SP3, SP4 or SP5 polynucleotide may be ligated to a heterologous sequence to encode a fusion protein. A fusion protein may also be engineered to contain a cleavage site located between the serine protease nucleotide sequence and the heterologous protein sequence, so that the serine protease may be cleaved and purified away from the heterologous moiety.

IV. Vector Sequences

Expression vectors used in expressing the serine proteases of the present invention in gram-positive microorganisms comprise at least one promoter associated with a serine protease selected from the group consisting of SP1, SP2, SP3, SP4 and SP5, which promoter is functional in the host cell. In one embodiment of the present invention, the promoter is the wild-type promoter for the selected serine protease and in another embodiment of the present invention, the promoter is heterologous to the serine protease, but still functional in the host cell. In one preferred embodiment of the present invention, nucleic acid encoding the serine protease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production of SP1, SP2, SP3, SP4 or SP5 including bacterial, fungal, mammalian and insects cells. General transformation procedures are taught in Current Protocols in Molecular Biology (vol. 1, edited by Ausubel et al., John Wiley & Sons, Inc. 1987, Chapter 9) and include calcium phosphate methods, transformation using DEAE-Dextran and electroporation. Plant transformation methods are taught in Rodriquez (WO 95/14099, published May 26, 1995).

In a preferred embodiment, the host cell is a gram-positive microorganism and in another preferred embodiment, the host cell is Bacillus. In one embodiment of the present invention, nucleic acid encoding one or more serine protease (s) of the present invention is introduced into a host cell via an expression vector capable of replicating within the host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a serine protease(s) of the present invention is stably integrated into the microorganism genome. Preferred host cells are gram-positive host cells. Another preferred host is Bacillus. Another preferred host is *Bacillus sublilis*. Several strategies have been described in the literature for the direct cloning of DNA in Bacillus. Plasmid marker rescue transformation involves the uptake of a donor plasmid by competent cells carrying a partially homologous resident plasmid (Contente et al., *Plasmid* 2:555–571 (1979); Haima et al., *Mol. Gen. Genet*. 223,185–191 (1990); Weinrauch et al., *J. Bacteriol*. 154(3):1077–1087 (1983); and Weinrauch et al., *J. Bacteriol*. 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B.megaterium* in Vorobjeva et al., (1980) FEMS Microbial. Letters 7:261–263; for *B. amyloliquefaciens* in Smith et al., (1986) Appl. and Env. Microbiol. 51:634; for *B.thuringiensis* in Fisher et al., (1981) Arch. Microbiol. 139:213–217; for *B.sphaericus* in McDonald (1984) J. Gen. Microbiol. 130:203; and *B.larvae* In Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes.

VI. Identification of Transformants

Whether a host cell has been transformed with a mutated or a naturally occurring gene encoding a gram-positive SP1, SP2, SP3, SP4 or SP5, detection of the presence/absence of marker gene expression can suggests whether the gene of interest is present However, its expression should be confirmed. For example, if the nucleic acid encoding a serine protease is inserted within a marker gene sequence, recombinant cells containing the insert can be identified by the absence of marker gene function. Alternatively, a marker gene can be placed in tandem with nucleic acid encoding the serine protease under the control of a single promoter. Expression of the marker gene in response to induction or selection usually indicates expression of the serine protease as well.

Alternatively, host cells which contain the coding sequence for a serine protease and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the cysteine polynucleotide sequence can be detected by DNA-DNA or DNA-RNA hybridization or amplification using probes, portions or fragments of *B.subtilis* SP1, SP2, SP3, SP4 or SP5.

VII. Assay of Protease Activity

There are various assays known to those of skill in the art for detecting and measuring protease activity. There are assays based upon the release of acid-soluble peptides from casein or hemoglobin measured as absorbance at 280 nm or colorimetrically using the Folin method (Bergmeyer, et al., 1984, Methods of Enzymatic Analysis vol. 5, Peptidases, Proteinases and their Inhibitors, Verlag Chemie, Weinheim). Other assays involve the solubilization of chromogenic substrates (Ward, 1983, Proteinases, in Microbial Enzymes and Biotechnology (W. M. Fogarty, ed.). Applied Science, London, pp. 251–317).

VIII. Secretion of Recombinant Proteins

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, *Serological Methods, a Laboratory Manual*, APS Press, St Paul, Minn.) and Maddox Del. et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.). Promega (Madison Wis.). and US Biochemical Corp (Cleveland, Ohio) supply commercial kits and protocols for these procedures. Suitable reporter molecules or labels include those radionuclides, enzymes, fluorescent, chemiluminescent, or chromogenic agent as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a serine protease of the present invention will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen, San Diego, Calif.) between the purification domain and the heterologous protein can be used to facilitate purification.

X. Uses of the Present Invention

Genetically Engineered Host Cells

The present invention provides genetically engineered host cells comprising preferably non-revertable mutations or deletions in the naturally occurring gene encoding one or more of SP1, SP2, SP3, SP4 or SP5 such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is genetically engineered to produce a desired protein or polypeptide. In a preferred embodiment the host cell is a Bacillus. In another preferred embodiment, the host cell is a *Bacillus subtilis.*

In an alternative embodiment, a host cell is genetically engineered to produce a gram-positive SP1, SP2, SP3, SP4 or SP5. In a preferred embodiment, the host cell is grown under large scale fermentation conditions, the SP1, SP2, SP3, SP4 or SP5 is isolated and/or purified and used in cleaning compositions such as detergents. WO 95/10615 discloses detergent formulation. A serine protease of the present invention can be useful in formulating various cleaning compositions. A number of known compounds are suitable surfactants useful in compositions comprising the serine protease of the invention. These include nonionic, anionic, cationic, anionic or zwitterionic detergents, as disclosed in U.S. Pat. No. 4,404,128 and U.S. Pat. No. 4,261,868. A suitable detergent formulation is that described in Example 7 of U.S. Pat. No. 5,204,015. The art is familiar with the different formulations which can be used as cleaning compositions. In addition, a serine protease of the present invention can be used, for example, in bar or liquid soap applications, dishcare formulations, contact lens cleaning solutions or products, peptide hydrolysis, waste treatment, textile applications, as fusion-cleavage enzymes in protein production, etc. A serine protease of the present invention may provide enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

A serine protease of the present invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of a serine protease to conventional cleaning compositions does not create any special use limitation. In other words, any temperature and pH suitable for the detergent is also suitable for the present compositions as long as the pH is within the above range, and the temperature is below the described serine protease denaturing temperature. In addition, a serine protease of the present invention can be used in a cleaning composition without detergents, again either alone or in combination with builders and stabilizers.

One aspect of the invention is a composition for the treatment of a textile that includes a serine protease of the present invention. The composition can be used to treat for example silk or wool as described in publications such as RD 216,034; EP 134,267; U.S. Pat. No. 4,533,359; and EP 344,259.

Proteases can be included in animal feed such as part of animal feed additives as described in, for example, U.S. Pat. No. 5,612,055; U.S. Pat. No. 5,314,692; and U.S. Pat. No. 5,147,642.

Polynucleotides

A *B.subtilis* SP1, SP2, SP3, SP4 or SP5 polynucleotide, or any part thereof, provides the basis for detecting the presence of gram-positive microorganism polynucleotide homologs through hybridization techniques and PCR technology.

Accordingly, one aspect of the present invention is to provide for nucleic acid hybridization and PCR probes which can be used to detect polynucleotide sequences, including genomic and cDNA sequences, encoding gram-positive SP1, SP2, SP3, SP4 or SP5 or portions thereof.

The manner and method of carrying out the present invention may be more fully understood by those of skill in the art by reference to the following examples, which examples are not intended in any manner to limit the scope of the present invention or of the claims directed thereto.

EXAMPLE I

Preparation of a Genomic Library

The following example illustrates the preparation of a Bacillus genomic library.

Genomic DNA from Bacillus cells is prepared as taught in Current Protocols In Molecular Biology vol. 1, edited by Ausubel et al., John Wiley & Sons, Inc. 1987, chapter 2 4.1.

Generally, Bacillus cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the Bacillus genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested Bacillus genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

The following example describes the detection of gram-positive microorganism SP1. The same procedures can be used to detect SP2, SP3, SP4 or SP5.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from SP1. A preferred probe comprises the nucleic acid section encoding conserved amino acid residues.

The nucleic acid probe is labeled by combining 50 pmol of the nucleic acid and 250 mCi of [gamma $^{32}P$] adenosine triphosphate (Amersham, Chicago, Ill.) and T4 polynucleotide kinase (DuPont NEN®, Boston, Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham, N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologs of *B.subtilis* SP1. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated in their entirety.

I claim:

1. A member of the genus Bacillus having a mutation or deletion of part or all of the gene encoding serine protase 1 (SP1), wherein said gene encoding serine protease 1 comprises SEQ ID NO: 1, said mutation or deletion resulting in the inactivaton of the SP1 proteolytic activity, and wherein said mutation or deletion is present in the catalytic triad sequence of said serine protease 1.

2. The microorganism according to claim 1, wherein the member is selected from the group consisting of *B. licheniformis, B. lentus, B. brevis, B. stearothermophilus, B. alkalophilus, B. amyloliquefaciens, B. coagulans, B. ciculans, B. lautus* and *Bacillus thuringiensis.*

3. The microorganism of claim 1 wherein said microorganism is capable of expressing a heterologous protein.

4. The microorganism of claim 3, wherein said heterologous protein is selected from the group consisting of hormones, enzymes, growth factors and cytokines.

5. The microorganism of claim 4 wherein said heterologous protein is an enzyme.

6. The microorganism of claim 5, wherein said enzyme is selected from the group consisting of proteases, carbohydrases, lipases, isomerases, racemases, epimerases, tautomerases, mutases, transferases, kinases, and phosphatases.

7. An expression vector comprising nucleic acid encoding SP1, wherein said SP1 comprises the nucleic acid sequence set forth in SEQ ID NO:1.

8. A host cell comprising an expression vector according to claim 7.

9. A method for the production of a heterologous protein in a Bacillus host cell comprising the steps of (a) obtaining a Bacillus host cell comprising nucleic acid encoding said heterologous protein wherein said host cell contains a mutation or deletion in the gene encoding serine protease 1, wherein said serine protease 1 comprises the nucleic acid sequence set forth in SEQ ID NO:1, and wherein said mutation or deletion is present in the catalytic triad sequence of said serine protease 1; and (b) growing said Bacillus host cell under conditions suitable for the expression of said heterologous protein.

10. The method of claim 9 wherein said Bacillus cell is selected from the group consisting of *Bacillus subtilis, B. licheniformis, B. lentus, B. brevis, B. stearothermophilus, B. alkalophilus, B. amyfoliquefaciens, B. coagulans, B. ciculans, B. lautus* and *Bacillus thuringiensis.*

11. The method of claim 10 wherein said Bacillus host cell further comprises a mutation or deletion in at least one of the genes encoding apr, npr, epr, wpr and mrp.

12. The microorganism of claim 1, further comprising a mutation or deletion in at least one of the genes encoding apr, npr, epr, wpr and mrp.

* * * * *

SEQUENCE LISTING

```
<160> NUMBER OF SEQ ID NOS: 10

<210> SEQ ID NO 1
<211> LENGTH: 1971
<212> TYPE: DNA
<213> ORGANISM: Bacillus subtilis

<400> SEQUENCE: 1

atgaaaaagc tgataaccgc agacgacatc acagcgattg tctctgtgac cgatcctcaa      60

tacgccccag acggtacccg tgccgcatat gtaaaatcac aagtaaatca agagaaagat     120

tcgtatacat caaatatatg gatctatgaa acgaaaacgg gaggatctgt tccttggaca     180

catggagaaa agcgaagcac cgacccaaga tggtctccgg acgggcgcac gcttgccttt     240

atttctgatc gagaaggcga tgcggcacag ctttatatca tgagcactga aggcggagaa     300

gcaagaaaac tgactgatat cccatatggc gtgtcaaagc cgctatggtc cccggacggt     360

gaatcgattc tggtcactat cagtttggga gagggggaaa gcattgatga ccgagaaaaa     420

acagagcagg acagctatga acctgttgaa gtgcaaggcc tctcctacaa acgggacggc     480

aaagggctga cgagaggtgc gtatgcccag cttgtgcttg tcagcgtaaa gtcgggtgag     540

atgaaagagc tgacaagtca caaagctgat catggtgatc ctgctttttc tcctgacggc     600

aaatggcttg ttttctcagc taatttaact gaaacagatg atgccagcaa gccgcatgat     660
```

-continued

```
gtttacataa tgtcactgga gtctggagat cttaagcagg ttacacctca tcgcggctca    720

ttcggatcaa gctcattttc accagacgga aggtatcttg ctttgcttgg aaatgaaaag    780

gaatataaga atgctacgct ctcaaaggcg tggctctatg atatcgaaca aggccgcctc    840

acatgtctta ctgagatgct ggacgttcat ttagcggatg cgctgattgg agattcattg    900

atcggtggtg ctgaacagcg cccgatttgg acaaaggaca gccaagggtt ttatgtcatc    960

ggcacagatc aaggcagtac gggcatctat tatatttcga ttgaaggcct tgtgtatccg   1020

attcgtctgg aaaaagagta catcaatagc ttttctcttt cacctgatga acagcacttt   1080

attgccagtg tgacaaagcc ggacagaccg agtgagcttt acagtatccc gcttggacag   1140

gaagagaaac agctgactgg cgcgaatgac aagtttgtca gggagcatac gatatcaata   1200

cctgaagaga ttcaatatgc tacagaagac ggcgtgatgg tgaacggctg gctgatgagg   1260

cctgcacaaa tggaaggtga gacaacatat ccacttattc ttaacataca cggcggtccg   1320

catatgatgt acggacatac atattttcat gagtttcagg tgctggcggc gaaaggatac   1380

gcggtcgttt atatcaatcc gagaggaagc cacggctacg ggcaggaatt tgtgaatgcg   1440

gtcagaggag attatggggg aaaggattat gacgatgtga tgcaggctgt ggatgaggct   1500

atcaaacgag atccgcatat tgatcctaag cggctcggtg tcacgggcgg aagctacgga   1560

ggttttatga ccaactggat cgtcgggcag acgaaccgct ttaaagctgc cgttacccag   1620

cgctcgatat caaattggat cagctttcac ggcgtcagtg atatcggcta tttctttaca   1680

gactggcagc ttgagcatga catgtttgag gacacagaaa agctctggga ccggtctcct   1740

ttaaaatacg cagcaaacgt ggagacaccg cttttgatac tgcatggcga gcgggatgac   1800

cgatgcccga tcgagcaggc ggagcagctg tttatcgctc tgaaaaaaat gggcaaggaa   1860

accaagcttg tccgttttcc gaatgcatcg cacaatttat cacgcaccgg acacccaaga   1920

cagcggatca agcgcctgaa ttatatcagc tcatggtttg atcaacatct c            1971
```

<210> SEQ ID NO 2
<211> LENGTH: 657
<212> TYPE: PRT
<213> ORGANISM: Bacillus subtilis

<400> SEQUENCE: 2

```
Met Lys Lys Leu Ile Thr Ala Asp Asp Ile Thr Ala Ile Val Ser Val
 1               5                  10                  15

Thr Asp Pro Gln Tyr Ala Pro Asp Gly Thr Arg Ala Ala Tyr Val Lys
            20                  25                  30

Ser Gln Val Asn Gln Glu Lys Asp Ser Tyr Thr Ser Asn Ile Trp Ile
        35                  40                  45

Tyr Glu Thr Lys Thr Gly Gly Ser Val Pro Trp Thr His Gly Glu Lys
    50                  55                  60

Arg Ser Thr Asp Pro Arg Trp Ser Pro Asp Gly Arg Thr Leu Ala Phe
65                  70                  75                  80

Ile Ser Asp Arg Glu Gly Asp Ala Ala Gln Leu Tyr Ile Met Ser Thr
                85                  90                  95

Glu Gly Gly Glu Ala Arg Lys Leu Thr Asp Ile Pro Tyr Gly Val Ser
            100                 105                 110

Lys Pro Leu Trp Ser Pro Asp Gly Glu Ser Ile Leu Val Thr Ile Ser
        115                 120                 125

Leu Gly Glu Gly Glu Ser Ile Asp Asp Arg Glu Lys Thr Glu Gln Asp
    130                 135                 140
```

-continued

```
Ser Tyr Glu Pro Val Glu Val Gln Gly Leu Ser Tyr Lys Arg Asp Gly
145                 150                 155                 160

Lys Gly Leu Thr Arg Gly Ala Tyr Ala Gln Leu Val Leu Val Ser Val
                165                 170                 175

Lys Ser Gly Glu Met Lys Glu Leu Thr Ser His Lys Ala Asp His Gly
            180                 185                 190

Asp Pro Ala Phe Ser Pro Asp Gly Lys Trp Leu Val Phe Ser Ala Asn
        195                 200                 205

Leu Thr Glu Thr Asp Asp Ala Ser Lys Pro His Asp Val Tyr Ile Met
    210                 215                 220

Ser Leu Glu Ser Gly Asp Leu Lys Gln Val Thr Pro His Arg Gly Ser
225                 230                 235                 240

Phe Gly Ser Ser Ser Phe Ser Pro Asp Gly Arg Tyr Leu Ala Leu Leu
                245                 250                 255

Gly Asn Glu Lys Glu Tyr Lys Asn Ala Thr Leu Ser Lys Ala Trp Leu
            260                 265                 270

Tyr Asp Ile Glu Gln Gly Arg Leu Thr Cys Leu Thr Glu Met Leu Asp
        275                 280                 285

Val His Leu Ala Asp Ala Leu Ile Gly Asp Ser Leu Ile Gly Gly Ala
    290                 295                 300

Glu Gln Arg Pro Ile Trp Thr Lys Asp Ser Gln Gly Phe Tyr Val Ile
305                 310                 315                 320

Gly Thr Asp Gln Gly Ser Thr Gly Ile Tyr Tyr Ile Ser Ile Glu Gly
                325                 330                 335

Leu Val Tyr Pro Ile Arg Leu Glu Lys Glu Tyr Ile Asn Ser Phe Ser
            340                 345                 350

Leu Ser Pro Asp Glu Gln His Phe Ile Ala Ser Val Thr Lys Pro Asp
        355                 360                 365

Arg Pro Ser Glu Leu Tyr Ser Ile Pro Leu Gly Gln Glu Glu Lys Gln
    370                 375                 380

Leu Thr Gly Ala Asn Asp Lys Phe Val Arg Glu His Thr Ile Ser Ile
385                 390                 395                 400

Pro Glu Glu Ile Gln Tyr Ala Thr Glu Asp Gly Val Met Val Asn Gly
                405                 410                 415

Trp Leu Met Arg Pro Ala Gln Met Glu Gly Glu Thr Thr Tyr Pro Leu
            420                 425                 430

Ile Leu Asn Ile His Gly Gly Pro His Met Met Tyr Gly His Thr Tyr
        435                 440                 445

Phe His Glu Phe Gln Val Leu Ala Ala Lys Gly Tyr Ala Val Val Tyr
    450                 455                 460

Ile Asn Pro Arg Gly Ser His Gly Tyr Gly Gln Glu Phe Val Asn Ala
465                 470                 475                 480

Val Arg Gly Asp Tyr Gly Gly Lys Asp Tyr Asp Asp Val Met Gln Ala
                485                 490                 495

Val Asp Glu Ala Ile Lys Arg Asp Pro His Ile Asp Pro Lys Arg Leu
            500                 505                 510

Gly Val Thr Gly Gly Ser Tyr Gly Gly Phe Met Thr Asn Trp Ile Val
        515                 520                 525

Gly Gln Thr Asn Arg Phe Lys Ala Ala Val Thr Gln Arg Ser Ile Ser
    530                 535                 540

Asn Trp Ile Ser Phe His Gly Val Ser Asp Ile Gly Tyr Phe Phe Thr
545                 550                 555                 560

Asp Trp Gln Leu Glu His Asp Met Phe Glu Asp Thr Glu Lys Leu Trp
```

-continued

```
                565                 570                 575

Asp Arg Ser Pro Leu Lys Tyr Ala Ala Asn Val Glu Thr Pro Leu Leu
            580                 585                 590

Ile Leu His Gly Glu Arg Asp Asp Arg Cys Pro Ile Glu Gln Ala Glu
        595                 600                 605

Gln Leu Phe Ile Ala Leu Lys Lys Met Gly Lys Glu Thr Lys Leu Val
    610                 615                 620

Arg Phe Pro Asn Ala Ser His Asn Leu Ser Arg Thr Gly His Pro Arg
625                 630                 635                 640

Gln Arg Ile Lys Arg Leu Asn Tyr Ile Ser Ser Trp Phe Asp Gln His
                645                 650                 655

Leu


<210> SEQ ID NO 3
<211> LENGTH: 818
<212> TYPE: PRT
<213> ORGANISM: Bacillus subtilis

<400> SEQUENCE: 3

Met Glu Gly Gly Glu Glu Glu Val Glu Arg Ile Pro Asp Glu Leu Phe
 1               5                  10                  15

Asp Thr Lys Lys Lys His Leu Leu Asp Lys Leu Ile Arg Val Gly Ile
            20                  25                  30

Ile Leu Val Leu Leu Ile Trp Gly Thr Val Leu Leu Leu Lys Ser Ile
        35                  40                  45

Pro His His Ser Asn Thr Pro Asp Tyr Gln Glu Pro Asn Ser Asn Tyr
    50                  55                  60

Thr Asn Asp Gly Lys Leu Lys Val Ser Phe Ser Val Val Arg Asn Asn
65                  70                  75                  80

Thr Phe Gln Pro Lys Tyr His Glu Leu Gln Trp Ile Ser Asp Asn Lys
                85                  90                  95

Ile Glu Ser Asn Asp Leu Gly Leu Tyr Val Thr Phe Met Asn Asp Ser
            100                 105                 110

Tyr Val Val Lys Ser Val Tyr Asp Asp Ser Tyr Asn Ser Val Leu Leu
        115                 120                 125

Glu Gly Lys Thr Phe Ile His Asn Gly Gln Asn Leu Thr Val Glu Ser
    130                 135                 140

Ile Thr Ala Ser Pro Asp Leu Lys Arg Leu Leu Ile Arg Thr Asn Ser
145                 150                 155                 160

Val Gln Asn Trp Arg His Ser Thr Phe Gly Ser Tyr Phe Val Tyr Asp
                165                 170                 175

Lys Ser Ser Ser Ser Phe Glu Glu Ile Gly Asn Glu Val Ala Leu Ala
            180                 185                 190

Ile Trp Ser Pro Asn Ser Asn Asp Ile Ala Tyr Val Gln Asp Asn Asn
        195                 200                 205

Ile Tyr Ile Tyr Ser Ala Ile Ser Lys Lys Thr Ile Arg Ala Val Thr
    210                 215                 220

Asn Asp Gly Ser Ser Phe Leu Phe Asn Gly Lys Pro Asp Trp Val Tyr
225                 230                 235                 240

Glu Glu Glu Val Phe Glu Asp Asp Lys Ala Ala Trp Trp Ser Pro Thr
                245                 250                 255

Gly Asp Tyr Leu Ala Phe Leu Lys Ile Asp Glu Ser Glu Val Gly Glu
            260                 265                 270

Phe Ile Ile Pro Tyr Tyr Val Gln Asp Glu Lys Asp Ile Tyr Pro Glu
```

-continued

```
        275                 280                 285

Met Arg Ser Ile Lys Tyr Pro Lys Ser Gly Thr Pro Asn Pro His Ala
    290                 295                 300

Glu Leu Trp Val Tyr Ser Met Lys Asp Gly Thr Ser Phe His Pro Arg
305                 310                 315                 320

Ile Ser Gly Asn Lys Lys Asp Gly Ser Leu Leu Ile Thr Glu Val Thr
                325                 330                 335

Trp Val Gly Asn Gly Asn Val Leu Val Lys Thr Thr Asp Arg Ser Ser
            340                 345                 350

Asp Ile Leu Thr Val Phe Leu Ile Asp Thr Ile Ala Lys Thr Ser Asn
        355                 360                 365

Val Val Arg Asn Glu Ser Ser Asn Gly Gly Trp Trp Glu Ile Thr His
    370                 375                 380

Asn Thr Leu Phe Ile Pro Ala Asn Glu Thr Phe Asp Arg Pro His Asn
385                 390                 395                 400

Gly Tyr Val Asp Ile Leu Pro Ile Gly Gly Tyr Asn His Leu Ala Tyr
                405                 410                 415

Phe Glu Asn Ser Asn Ser Ser His Tyr Lys Thr Leu Thr Glu Gly Lys
            420                 425                 430

Trp Glu Val Val Asn Gly Pro Leu Ala Phe Asp Ser Met Glu Asn Arg
        435                 440                 445

Leu Tyr Phe Ile Ser Thr Arg Lys Ser Ser Thr Glu Arg His Val Tyr
    450                 455                 460

Tyr Ile Asp Leu Arg Ser Pro Asn Glu Ile Ile Glu Val Thr Asp Thr
465                 470                 475                 480

Ser Glu Asp Gly Val Tyr Asp Val Ser Phe Ser Ser Gly Arg Arg Phe
                485                 490                 495

Gly Leu Leu Thr Tyr Lys Gly Pro Lys Val Pro Tyr Gln Lys Ile Val
            500                 505                 510

Asp Phe His Ser Arg Lys Ala Glu Lys Cys Asp Lys Gly Asn Val Leu
        515                 520                 525

Gly Lys Ser Leu Tyr His Leu Glu Lys Asn Glu Val Leu Thr Lys Ile
    530                 535                 540

Leu Glu Asp Tyr Ala Val Pro Arg Lys Ser Phe Arg Glu Leu Asn Leu
545                 550                 555                 560

Gly Lys Asp Glu Phe Gly Lys Asp Ile Leu Val Asn Ser Tyr Glu Ile
                565                 570                 575

Leu Pro Asn Asp Phe Asp Glu Thr Leu Ser Asp His Tyr Pro Val Phe
            580                 585                 590

Phe Phe Ala Tyr Gly Gly Pro Asn Ser Gln Gln Val Val Lys Thr Phe
        595                 600                 605

Ser Val Gly Phe Asn Glu Val Val Ala Ser Gln Leu Asn Ala Ile Val
    610                 615                 620

Val Val Val Asp Gly Arg Gly Thr Gly Phe Lys Gly Gln Asp Phe Arg
625                 630                 635                 640

Ser Leu Val Arg Asp Arg Leu Gly Asp Tyr Glu Ala Arg Asp Gln Ile
                645                 650                 655

Ser Ala Ala Ser Leu Tyr Gly Ser Leu Thr Phe Val Asp Pro Gln Lys
            660                 665                 670

Ile Ser Leu Phe Gly Trp Ser Tyr Gly Gly Tyr Leu Thr Leu Lys Thr
        675                 680                 685

Leu Glu Lys Asp Gly Gly Arg His Phe Lys Tyr Gly Met Ser Val Ala
    690                 695                 700
```

-continued

```
Pro Val Thr Asp Trp Arg Phe Tyr Asp Ser Val Tyr Thr Glu Arg Tyr
705                 710                 715                 720

Met His Thr Pro Gln Glu Asn Phe Asp Gly Tyr Val Glu Ser Ser Val
                725                 730                 735

His Asn Val Thr Ala Leu Ala Gln Ala Asn Arg Phe Leu Leu Met His
            740                 745                 750

Gly Thr Gly Asp Asp Asn Val His Phe Gln Asn Ser Leu Lys Phe Leu
        755                 760                 765

Asp Leu Leu Asp Leu Asn Gly Val Glu Asn Tyr Asp Val His Val Phe
    770                 775                 780

Pro Asp Ser Asp His Ser Ile Arg Tyr His Asn Ala Asn Val Ile Val
785                 790                 795                 800

Phe Asp Lys Leu Leu Asp Trp Ala Lys Arg Ala Phe Asp Gly Gln Phe
                805                 810                 815

Val Lys


<210> SEQ ID NO 4
<211> LENGTH: 771
<212> TYPE: DNA
<213> ORGANISM: Bacillius subtilis

<400> SEQUENCE: 4

ttgattgtag agaaaagaag atttccgtcg ccaagccagc atgtgcgttt gtatacgatc      60

tgctatctgt caaatggatt acgggttaag ggcttctgg ctgagccggc ggaaccggga     120

caatatgacg gatttttata tttgcgcggc gggattaaaa gcgtgggcat ggttcggccg     180

ggccggatta tccagtttgc atcccaaggg tttgtggtgt ttgctccttt ttacagaggc     240

aatcaaggag gagaaggcaa tgaggatttt gccggagaag acagggagga tgcatttttct     300

gcttttcgcc tgcttcagca gcacccaaat gtcaagaagg atagaatcca tatcttcggt     360

ttttcccgcg gcggaattat gggaatgctc actgcgatcg aaatgggcgg gcaggcagct     420

tcatttgttt cctggggagg cgtcagtgat atgattctta catacgagga gcggcaggat     480

ttgcggcgaa tgatgaaaag agtcatcggc ggaacaccga aaaaggtgcc tgaggaatat     540

caatggagga caccgtttga ccaagtaaac aaaattcagg ctcccgtgct gttaatccat     600

ggagaaaaag accaaaatgt ttcgattcag cattcctatt tattagaaga gaagctaaaa     660

caactgcata agccggtgga aacatggtac tacagtacat tcacacatta tttcccgcca     720

aaagaaaacc ggcgtatcgt gcggcagctc acacaatgga tgaaaaaccg c             771


<210> SEQ ID NO 5
<211> LENGTH: 257
<212> TYPE: PRT
<213> ORGANISM: Bacillus subtilis

<400> SEQUENCE: 5

Met Ile Val Glu Lys Arg Arg Phe Pro Ser Pro Ser Gln His Val Arg
 1               5                  10                  15

Leu Tyr Thr Ile Cys Tyr Leu Ser Asn Gly Leu Arg Val Lys Gly Leu
            20                  25                  30

Leu Ala Glu Pro Ala Glu Pro Gly Gln Tyr Asp Gly Phe Leu Tyr Leu
        35                  40                  45

Arg Gly Gly Ile Lys Ser Val Gly Met Val Arg Pro Gly Arg Ile Ile
    50                  55                  60

Gln Phe Ala Ser Gln Gly Phe Val Val Phe Ala Pro Phe Tyr Arg Gly
```

-continued

```
65                  70                  75                  80

Asn Gln Gly Gly Glu Gly Asn Glu Asp Phe Ala Gly Glu Asp Arg Glu
                85                  90                  95

Asp Ala Phe Ser Ala Phe Arg Leu Leu Gln Gln His Pro Asn Val Lys
            100                 105                 110

Lys Asp Arg Ile His Ile Phe Gly Phe Ser Arg Gly Gly Ile Met Gly
        115                 120                 125

Met Leu Thr Ala Ile Glu Met Gly Gly Gln Ala Ala Ser Phe Val Ser
    130                 135                 140

Trp Gly Gly Val Ser Asp Met Ile Leu Thr Tyr Glu Glu Arg Gln Asp
145                 150                 155                 160

Leu Arg Arg Met Met Lys Arg Val Ile Gly Gly Thr Pro Lys Lys Val
                165                 170                 175

Pro Glu Glu Tyr Gln Trp Arg Thr Pro Phe Asp Gln Val Asn Lys Ile
            180                 185                 190

Gln Ala Pro Val Leu Leu Ile His Gly Glu Lys Asp Gln Asn Val Ser
        195                 200                 205

Ile Gln His Ser Tyr Leu Leu Glu Glu Lys Leu Lys Gln Leu His Lys
    210                 215                 220

Pro Val Glu Thr Trp Tyr Tyr Ser Thr Phe Thr His Tyr Phe Pro Pro
225                 230                 235                 240

Lys Glu Asn Arg Arg Ile Val Arg Gln Leu Thr Gln Trp Met Lys Asn
                245                 250                 255

Arg
```

<210> SEQ ID NO 6
<211> LENGTH: 765
<212> TYPE: DNA
<213> ORGANISM: Bacillus subtilis

<400> SEQUENCE: 6

```
gtgatacaaa ttgagaatca aaccgtttcc ggtattccgt ttttacatat tgtaaaggaa     60

gagaacaggc accgcgctgt tcctctcgtg atctttatac atggttttac aagcgcgaag    120

gaacacaacc ttcatattgc ttatctgctt gcggagaagg gttttagagc cgttctgccg    180

gaggctttgc accatgggga acggggagaa gaaatggctg ttgaagagct ggcggggcat    240

ttttgggata tcgtcctcaa cgagattgaa gagatcggcg tacttaaaaa ccattttgaa    300

aaagagggcc tgatagacgg cggccgcatc ggtctcgcag gcacgtcaat gggcggcatc    360

acaacgcttg gcgctttgac tgcatatgat tggataaaag ccggcgtcag cctgatggga    420

agcccgaatt acgtggagct gtttcagcag cagattgacc atattcaatc tcagggcatt    480

gaaatcgatg tgccggaaga gaaggtacag cagctgatga aacgtctcga gttgcgggat    540

ctcagccttc agccggagaa actgcaacag cgcccgcttt tattttggca cggcgcaaaa    600

gataaagttg tgccttacgc gccgacccgg aaattttatg acacgattaa atcccattac    660

agcgagcagc cggaacgcct gcaatttatc ggagatgaaa acgctgacca taaagtcccg    720

cgggcagctg tgttaaaaac gattgaatgg tttgaaacgt actta                    765
```

<210> SEQ ID NO 7
<211> LENGTH: 255
<212> TYPE: PRT
<213> ORGANISM: Bacillus subtilis

<400> SEQUENCE: 7

-continued

```
Met Ile Gln Ile Glu Asn Gln Thr Val Ser Gly Ile Pro Phe Leu His
 1               5                  10                  15

Ile Val Lys Glu Glu Asn Arg His Arg Ala Val Pro Leu Val Ile Phe
            20                  25                  30

Ile His Gly Phe Thr Ser Ala Lys Glu His Asn Leu His Ile Ala Tyr
        35                  40                  45

Leu Leu Ala Glu Lys Gly Phe Arg Ala Val Leu Pro Glu Ala Leu His
    50                  55                  60

His Gly Glu Arg Gly Glu Glu Met Ala Val Glu Glu Leu Ala Gly His
65                  70                  75                  80

Phe Trp Asp Ile Val Leu Asn Glu Ile Glu Glu Ile Gly Val Leu Lys
                85                  90                  95

Asn His Phe Glu Lys Glu Gly Leu Ile Asp Gly Gly Arg Ile Gly Leu
            100                 105                 110

Ala Gly Thr Ser Met Gly Gly Ile Thr Thr Leu Gly Ala Leu Thr Ala
        115                 120                 125

Tyr Asp Trp Ile Lys Ala Gly Val Ser Leu Met Gly Ser Pro Asn Tyr
    130                 135                 140

Val Glu Leu Phe Gln Gln Gln Ile Asp His Ile Gln Ser Gln Gly Ile
145                 150                 155                 160

Glu Ile Asp Val Pro Glu Glu Lys Val Gln Gln Leu Met Lys Arg Leu
                165                 170                 175

Glu Leu Arg Asp Leu Ser Leu Gln Pro Glu Lys Leu Gln Gln Arg Pro
            180                 185                 190

Leu Leu Phe Trp His Gly Ala Lys Asp Lys Val Val Pro Tyr Ala Pro
        195                 200                 205

Thr Arg Lys Phe Tyr Asp Thr Ile Lys Ser His Tyr Ser Glu Gln Pro
    210                 215                 220

Glu Arg Leu Gln Phe Ile Gly Asp Glu Asn Ala Asp His Lys Val Pro
225                 230                 235                 240

Arg Ala Ala Val Leu Lys Thr Ile Glu Trp Phe Glu Thr Tyr Leu
                245                 250                 255
```

<210> SEQ ID NO 8
<211> LENGTH: 915
<212> TYPE: DNA
<213> ORGANISM: Bacillus subtilis

<400> SEQUENCE: 8

```
ttgaagaaaa tccttttggc cattggcgcg ctcgtaacag ctgtcatcgc aatcggaatt     60

gtttttttcac atatgattct attcatcaag aaaaaaacgg atgaagacat tatcaaaaga    120

gagacagaca acggacatga tgtgtttgaa tcatttgaac aaatggagaa aaccgctttt    180

gtgataccct ccgcttacgg gtacgacata aaaggatacc atgtcgcacc gcatgacaca    240

ccaaatacca tcatcatctg ccacggggtg acgatgaatg tactgaattc tcttaagtat    300

atgcatttat ttctagatct cggctggaat gtgctcattt atgaccatcg ccggcatggc    360

caaagcggcg gaaagacgac cagctacggg ttttacgaaa aggatgatct caataaggtt    420

gtcagcttgc tcaaaaacaa aacaaatcat cgcggattga tcggaattca tggtgagtcg    480

atgggggccg tgaccgccct gctttatgct ggtgcacact gcagcgatgg cgctgatttt    540

tatattgccg attgtccgtt cgcatgtttt gatgaacagc ttgcctatcg gctgagagcg    600

gaatacaggc tcccgtcttg gcccctgctt cctatcgccg acttcttttt gaagctgagg    660

ggaggctatc gcgcacgtga agtatctccg cttgctgtca ttgataaaat tgaaaagccg    720
```

-continued gtcctcttta ttcacagtaa ggatgatgac tacattcctg tttcttcaac cgagcggctt 780
tatgaaaaga aacgcggtcc gaaagcgctg tacattgccg agaacggtga acacgccatg 840
tcatatacca aaaatcggca tacgtaccga aaaacagtgc aggagttttt agacaacatg 900
aatgattcaa cagaa 915

<210> SEQ ID NO 9
<211> LENGTH: 305
<212> TYPE: PRT
<213> ORGANISM: Bacillus subtilis

<400> SEQUENCE: 9

Met Lys Lys Ile Leu Leu Ala Ile Gly Ala Leu Val Thr Ala Val Ile
1 5 10 15

Ala Ile Gly Ile Val Phe Ser His Met Ile Leu Phe Ile Lys Lys Lys
20 25 30

Thr Asp Glu Asp Ile Ile Lys Arg Glu Thr Asp Asn Gly His Asp Val
35 40 45

Phe Glu Ser Phe Glu Gln Met Glu Lys Thr Ala Phe Val Ile Pro Ser
50 55 60

Ala Tyr Gly Tyr Asp Ile Lys Gly Tyr His Val Ala Pro His Asp Thr
65 70 75 80

Pro Asn Thr Ile Ile Ile Cys His Gly Val Thr Met Asn Val Leu Asn
85 90 95

Ser Leu Lys Tyr Met His Leu Phe Leu Asp Leu Gly Trp Asn Val Leu
100 105 110

Ile Tyr Asp His Arg Arg His Gly Gln Ser Gly Gly Lys Thr Thr Ser
115 120 125

Tyr Gly Phe Tyr Glu Lys Asp Asp Leu Asn Lys Val Val Ser Leu Leu
130 135 140

Lys Asn Lys Thr Asn His Arg Gly Leu Ile Gly Ile His Gly Glu Ser
145 150 155 160

Met Gly Ala Val Thr Ala Leu Leu Tyr Ala Gly Ala His Cys Ser Asp
165 170 175

Gly Ala Asp Phe Tyr Ile Ala Asp Cys Pro Phe Ala Cys Phe Asp Glu
180 185 190

Gln Leu Ala Tyr Arg Leu Arg Ala Glu Tyr Arg Leu Pro Ser Trp Pro
195 200 205

Leu Leu Pro Ile Ala Asp Phe Phe Leu Lys Leu Arg Gly Gly Tyr Arg
210 215 220

Ala Arg Glu Val Ser Pro Leu Ala Val Ile Asp Lys Ile Glu Lys Pro
225 230 235 240

Val Leu Phe Ile His Ser Lys Asp Asp Asp Tyr Ile Pro Val Ser Ser
245 250 255

Thr Glu Arg Leu Tyr Glu Lys Lys Arg Gly Pro Lys Ala Leu Tyr Ile
260 265 270

Ala Glu Asn Gly Glu His Ala Met Ser Tyr Thr Lys Asn Arg His Thr
275 280 285

Tyr Arg Lys Thr Val Gln Glu Phe Leu Asp Asn Met Asn Asp Ser Thr
290 295 300

Glu
305

<210> SEQ ID NO 10

-continued

```
<211> LENGTH: 318
<212> TYPE: PRT
<213> ORGANISM: Bacillus subtilis

<400> SEQUENCE: 10

Met Gln Leu Phe Asp Leu Pro Leu Asp Gln Leu Gln Thr Tyr Lys Pro
 1               5                  10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```